United States Patent
Sadowski et al.

(10) Patent No.: US 9,364,449 B2
(45) Date of Patent: Jun. 14, 2016

(54) PEPTOID AND SYNTHETIC OLIGOMERS, PHARMACEUTICAL COMPOSITIONS AND METHODS OF USING SAME

(75) Inventors: Martin J. Sadowski, New York, NY (US); Kent Kirshenbaum, New York, NY (US)

(73) Assignee: New York University, New York, NY (US)

( * ) Notice: Subject to any disclaimer, the term of this patent is extended or adjusted under 35 U.S.C. 154(b) by 873 days.

(21) Appl. No.: 13/134,547

(22) Filed: Jun. 9, 2011

(65) Prior Publication Data
US 2012/0015883 A1  Jan. 19, 2012

(51) Int. Cl.
A61K 38/08 (2006.01)
A61K 38/12 (2006.01)
A61K 38/16 (2006.01)
C07K 7/06 (2006.01)
C07K 7/64 (2006.01)
(Continued)

(52) U.S. Cl.
CPC .............. A61K 31/135 (2013.01); A61K 38/08 (2013.01); A61K 38/12 (2013.01); A61K 38/16 (2013.01); C07K 7/06 (2013.01); C07K 7/64 (2013.01); C07K 14/00 (2013.01)

(58) Field of Classification Search
None
See application file for complete search history.

(56) References Cited

U.S. PATENT DOCUMENTS 6,303,567 B1 * 10/2001 Findeis et al. ............... 514/17.7
7,125,838 B1  10/2006 Stott (Continued)

FOREIGN PATENT DOCUMENTS

WO  WO 2007145589 A1 * 12/2007
WO  WO 2008022800 A1 *  2/2008
(Continued)

OTHER PUBLICATIONS

Simon et al., "Peptoids: A modular approach to drug discovery", Proc Natl Acad Sci USA, 1992, vol. 89, pp. 9367-9371.
(Continued)

*Primary Examiner* — Jeffrey E Russel
(74) *Attorney, Agent, or Firm* — Klauber & Jackson LLC

(57) ABSTRACT

Novel peptide/peptoid oligomers are disclosed that have a formula represented by the following formula Ia or Ib:

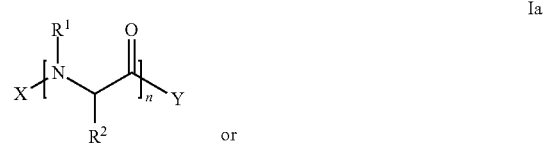

or

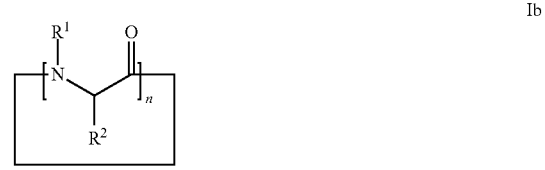

The peptide/peptoid oligomers demonstrate the ability to inhibit fibrillization and oligomerization of Aβ and may be prepared as pharmaceutical compositions and used for the prevention or treatment of a variety of conditions in mammals, including humans, associated with Aβ oligomerization. The present peptidomimetic oligomers are particularly valuable for the treatment of subjects with AD.

21 Claims, 9 Drawing Sheets

(51) Int. Cl.
  *C07K 14/00* (2006.01)
  *A61K 31/135* (2006.01)

(56) References Cited

U.S. PATENT DOCUMENTS

| | | | |
|---|---|---|---|
| 8,524,663 B2* | 9/2013 | Kirshenbaum et al. | 514/9.7 |
| 8,658,677 B2 | 2/2014 | Almassian et al. | |
| 8,828,413 B2 | 9/2014 | Kirshenbaum et al. | |
| 2004/0029811 A1 | 2/2004 | Orts et al. | |
| 2004/0254099 A1 | 12/2004 | Blaschuk et al. | |
| 2007/0081998 A1 | 4/2007 | Kinney et al. | |
| 2008/0107649 A1 | 5/2008 | Zurbriggen | |
| 2009/0305946 A1 | 12/2009 | Dewji et al. | |
| 2009/0318667 A1* | 12/2009 | Kirshenbaum et al. | 530/329 |
| 2010/0222255 A1* | 9/2010 | Kirshenbaum et al. | 514/9 |
| 2010/0222548 A1* | 9/2010 | Wessjohann et al. | 530/328 |
| 2011/0092445 A1 | 4/2011 | Barghorn et al. | |
| 2014/0100354 A1 | 4/2014 | Kirshenbaum et al. | |
| 2014/0113862 A1 | 4/2014 | Kirshenbaum et al. | |
| 2014/0274916 A1 | 9/2014 | Kirshenbaum et al. | |
| 2015/0011465 A1 | 1/2015 | Kirshenbaum et al. | |
| 2015/0044189 A1 | 2/2015 | Kirshenbaum et al. | |

FOREIGN PATENT DOCUMENTS

| | | |
|---|---|---|
| WO | 2008134034 | 11/2008 |
| WO | 2013158600 | 10/2013 |

OTHER PUBLICATIONS

Bose et al., "Poly-N-methylated amyloid beta-peptide (A beta) C-terminal fragments reduce A beta toxicity in vitro and in *Drosophila melanogaster*", Journal of Medicinal Chemistry, 2009, vol. 52, pp. 8002-8009.

Cruz et al., "Inhibition of beta-amyloid toxicity by short peptides containing N-methyl amino acids", Journal of Peptide Research, 2004, vol. 63, pp. 324-328.

Huang et al., Recombinant GST-I-A beta-28-induced efficient serum antibody against A beta B42, Journal of Neuroscience Methods, 2010, vol. 186, pp. 52-59.

Doig et al., "Inhibition of toxicity and protofibril formation in the amyloid-beta peptide beta(25-35) using N-methylated derivatives", Biochemical Society Transactions, 2002, vol. 30, pp. 537-542.

Elgersma et al., "Transformation of the amyloidogenic peptide amylin (20-29) into its corresponding peptoid and retropeptoid: Access to both an amyloid inhibitor and template for self-assembled supramolecular tapes", Bioorganic & Medicinal Chemistry Letters, 2007, vol. 17, pp. 1837-1842.

Figliozzi et al., "Synthesis of N-substituted glycine peptoid libraries", Methods Enzymol, 1996, vol. 267, pp. 437-447.

Golabek et al., "The interaction between apolipoprotein E and Alzheimer's amyloid beta-peptide is dependent on beta-peptide conformation", J Biol Chem, 1996, vol. 271, pp. 10602-10606.

Gordon et al., "Inhibition of beta-amyloid(40) fibrillogenesis and disassembly of beta-amyloid (40) fibrils by short beta-amyloid congeners containing N-methyl amino acids at alternate residues", Biochemistry, 2001, vol. 40, pp. 8237-8245.

Gordon et al., "Design and characterization of a membrane permeable N-methyl amino acid-containing peptide that inhibits A beta1-40 fibrillogenesis", Journal of Peptide Research, 2002, vol. 60, pp. 37-55.

Grillo-Bosch et al., "Retro-enantio N-methylated peptides as beta-amyloid aggregation inhibitors", ChemMedChem, 2009, vol. 4, pp. 1488-1494.

Kokkoni et al., "N-methylated peptide inhibitors of beta-amyloid aggregation and toxicity. Optimization of the inhibitor structure", Biochemistry, 2006, vol. 45, pp. 9906-9918.

Li et al., "Contrasting in vivo effects of two peptide-based amyloid-beta protein aggregation inhibitors in a transgenic mouse model of amyloid deposition", Cell Transplantation, 2008, vol. 17, pp. 397-408.

Ovadia et al., "The effect of backbone cyclization on PK/PD properties of bioactive peptide-peptoid hybrids: The melanocortin agonist paradigm", Bioorganic & Medicinal Chemistry, 2010, vol. 18, pp. 580-589.

Sciarretta et al., "Peptide-based inhibitors of amyloid assembly", Methods in Enzymology, 2006, vol. 413, pp. 273-312.

Sciarretta et al., "Spatial separation of beta-sheet domains of beta-amyloid: Disruption of each beta-sheet by N-methyl amino acids", Biochemistry, 2006, vol. 45, pp. 9485-9495.

Soto et al., "New insights into the mechanism of Alzheimer amyloid-beta fibrillogenesis inhibition by N-methylated peptides", Biophysical Journal, 2007, vol. 93, pp. 3015-3025.

Riviere et al. "The polyphenol piceid destabilizes preformed amyloid fibrils and oligomers in vitro: Hypothesis on possible molecular mechanisms", Neurochemical Research, 2009, vol. 34, pp. 1120-1128.

Sadowski et al., "Anti-PrP Mab 6D11 suppresses PrPSc replication in prion infected myeloid precursor line FDC-P1/22L and in the lymphoreticular system in vivo", Neurobiol Dis, 2009, vol. 34, pp. 267-278.

Sadowski et al., "A synthetic peptide blocking the apolipoprotein E/beta-amyloid binding mitigates beta-amyloid toxicity and fibril formation in vitro and reduces beta-amyloid plaques in transgenic mice", Am J Pathol, 2004, vol. 165, pp. 937-948.

Sadowski et al., "Blocking the apolipoprotein E/amyloid-beta interaction as a potential therapeutic approach for Alzheimer's disease", Proc Natl Acad Sci USA, 2006, vol. 103, pp. 18787-18792.

Sadowski et al., "Amyloid-beta deposition is associated with decreased hippocampal glucose metabolism and spatial memory impairment in APP/PS1 mice", J Neuropath Exp Neurol, 2004, vol. 63, pp. 418-428.

Sadowski et al., "Targeting prion amyloid deposits in vivo", J Neuropath Exp Neurol, 2004, vol. 63, pp. 775-784.

Stine et al., "In vitro characterization of conditions for amyloid-beta peptide oligomerization and fibrillogenesis", J Biol Chem, 2003, vol. 278, pp. 11612-11622.

Sigurdsson et al., "A non-toxic ligand for voxel-based MRI analysis of plaques in AD transgenic mice", Neurobiology of Aging, 2008, vol. 29, pp. 836-847.

Kayed et al., "Common structure of soluble amyloid oligomers implies common mechanism of pathogenesis", Science, 2003, vol. 300, pp. 486-489.

Taylor et al., "Development of a proteolytically stable retro-inverso peptide inhibitor of beta-amyloid oligomerization as a potential novel treatment for Alzheimer's Disease", Biochemistry, 2010, vol. 49, pp. 3261-3272.

Zuckermann et al., "Peptoids as potential therapeutics", Current Opinion in Molecular Therapeutics, 2009, vol. 11, pp. 299-307.

Zuckermann et al., "Efficient method for the preparation of peptoids [oligo(n-substituted glycines)] by submonomer solid-phase synthesis", J Am Chem Soc, 1992, vol. 114, pp. 10646-10647.

* cited by examiner

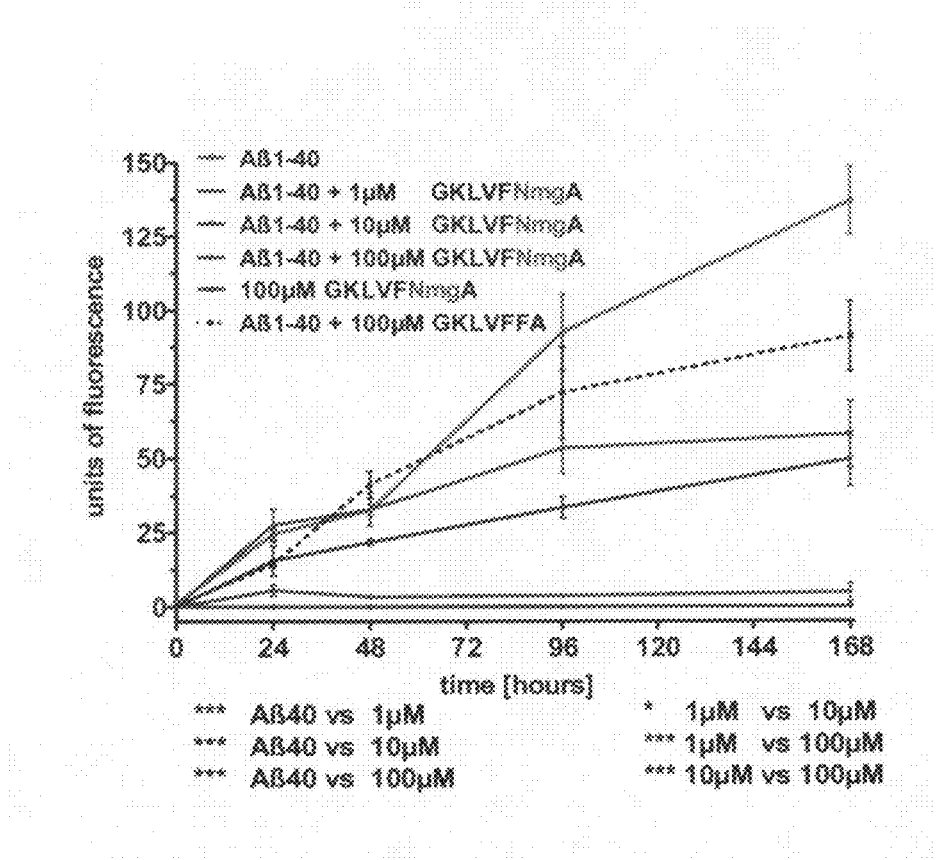

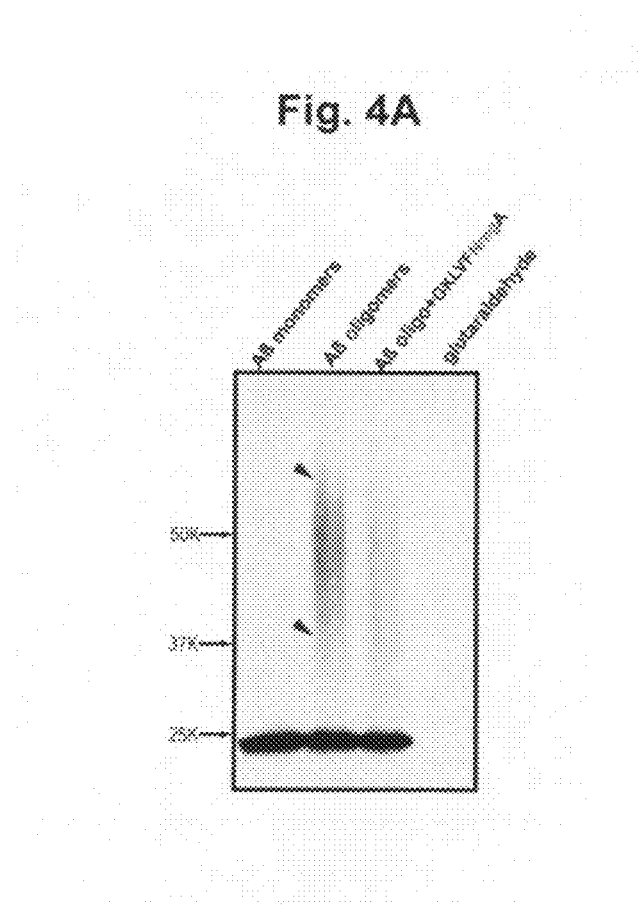
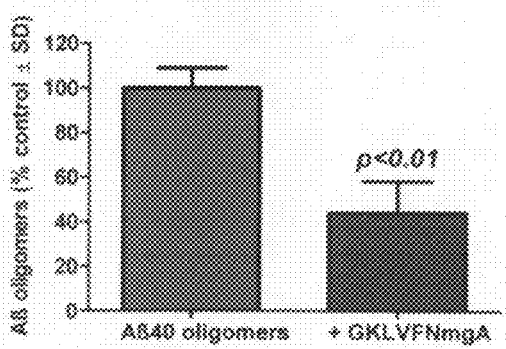

Fig. 5
Panel I
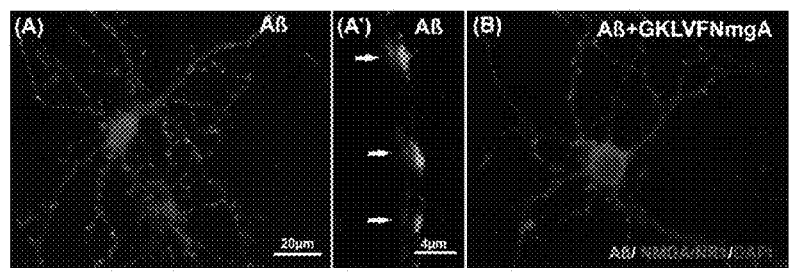
Panel II
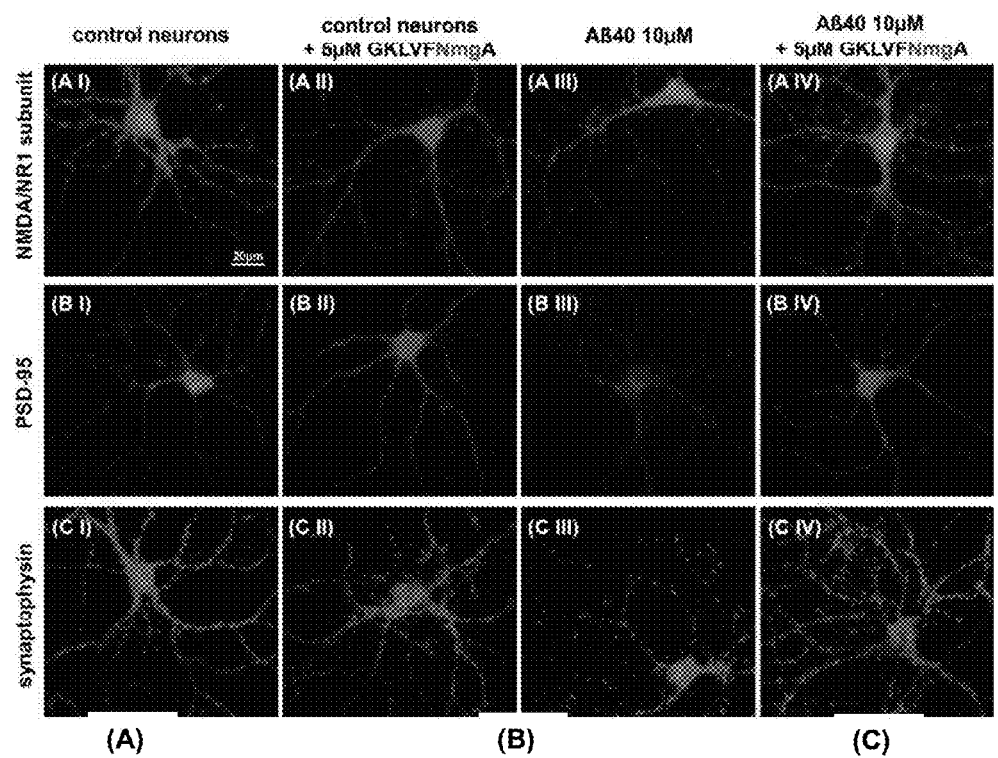

Fig. 5 (Contd)
Panel III
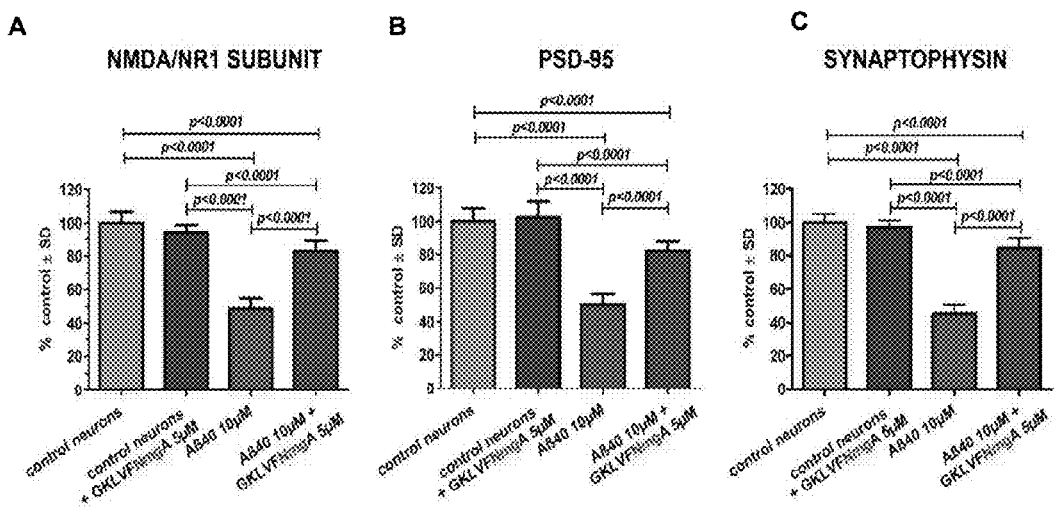

Fig. 8
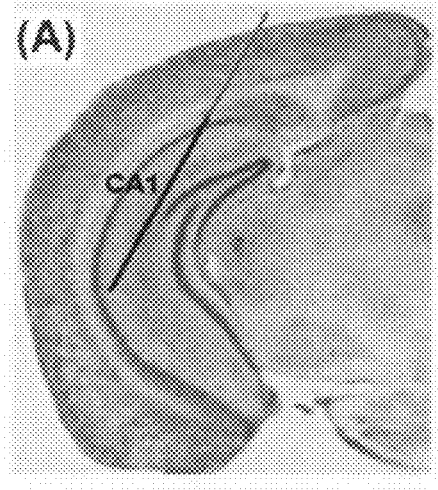
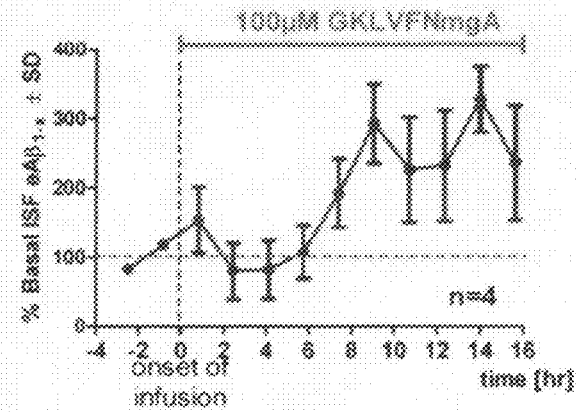

PEPTOID AND SYNTHETIC OLIGOMERS, PHARMACEUTICAL COMPOSITIONS AND METHODS OF USING SAME

GOVERNMENT RIGHTS

The research leading to the present invention was funded in part by NIH grants R01 AG 031221, R01 AG 031221-03S1, and 1K02AG034176-01 and a NSF CAREER grant #0645361. Accordingly, the United States government has certain rights in the invention.

CROSS REFERENCE TO RELATED APPLICATIONS

This application claims priority under 35 USC §119(e) from U.S Provisional Application Ser. No. 61/397,290, filed Jun. 9, 2010, which application is herein specifically

FIELD OF THE INVENTION

This invention relates to novel compositions containing active peptoid or synthetic oligomers (peptidomimetic oligomers), and particularly, use of such peptidomimetic oligomers in therapy for Alzheimer's disease (AD). The invention generally relates to use of peptidomimetic oligomers and compositions thereof in pharmaceutical, healthcare, and medical device applications.

BACKGROUND OF THE INVENTION

Alzheimer's disease (AD) is the most common cause of dementia and there are no therapeutics effectively addressing the pathomechanism of this disease. The prevalence of AD is estimated to be 5.3 million cases in the USA (Alzheimer's Association 2009) and over 25 million cases worldwide. The prevalence of the disease is, moreover, expected to rise with the increasing average age of the global population. AD is caused by progressive accumulation of a toxic and hydrophobic β-amyloid (Aβ) peptide in the brain, which gradually effects loss of synapses, occurrence of neurofibrillary pathology, neuronal loss and eventually invokes symptoms of dementia. Accumulation of Aβ in the brain is driven by the inherent hydrophobicity of Aβ and its natural propensity to self-aggregate into toxic oligomers and fibers. Transgenic mice overexpressing human amyloid precursor protein mutant alone or together with a mutant of human presenilin 1 model early AD pathology and demonstrate profound memory impairment, which correlates with the presence of Aβ oligomers in the brain targeting NMDA receptors, but precedes timing of Aβ plaque formation. Despite the existing wealth of evidence pointing toward the deleterious effect of Aβ and Aβ oligomeric species in particular, there are no therapeutics available that effectively target the pathomechanism of AD.

Thus, there is an on-going need for development of effective therapeutic agents that target mechanisms of Aβ accumulation and toxicity in AD patients.

SUMMARY OF THE INVENTION

In an effort to generate therapeutic agents for the treatment of AD, the present inventors have designed and synthesized libraries of non-toxic, biostable peptoid or synthetic oligomer antagonists of Aβ fibrillization and oligomerization and tested same in vitro and in vivo. As described herein, exemplary biostable peptoid or synthetic oligomer antagonists have been shown to exhibit improved pharmacokinetic profiles as compared to analogous peptides.

As demonstrated herein, peptoid or synthetic oligomers (peptidomimetic oligomers) of the present invention also prevent loss of glutamatergic NMDA receptors and other synaptic proteins and ameliorate intraneuronal Aβ accumulation. These findings lead to novel peptoid or synthetic oligomers that are promising candidates for therapeutic use. It also leads to pharmaceutical compositions comprising the peptidomimetic oligomers of the present invention as active ingredients and to their use to treat, prevent or ameliorate AD.

The peptoid or synthetic oligomer antagonists of Aβ fibrillization and oligomerization exhibit enhanced stability, due, at least in part, to resistance to enzymatic digestion. This property imparts to the peptoid or synthetic oligomer antagonists the potential for use in therapeutic compositions, particularly those designed for oral administration. The peptoid or synthetic oligomer antagonists of the invention are also expected to exhibit improved blood-brain-barrier permeability.

More particularly, the present invention relates to peptide/peptoid oligomers or synthetic oligomers having the ability to inhibit oligomerization and fibrillization of Aβ, according to formula Ia or Ib:

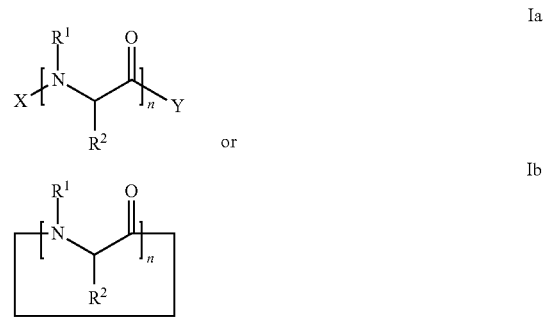

wherein
each $R^1$ is independently H, substituted or unsubstituted alkyl, substituted or unsubstituted cycloalkyl, substituted or unsubstituted aralkyl, substituted or unsubstituted cycloalkylalkyl, substituted or unsubstituted aryl, or substituted or unsubstituted heteroaryl;
each $R^2$ is independently hydrogen, or substituted or unsubstituted alkyl;
n is an integer between 2-45, when the synthetic oligomer is of formula Ia; and n is an integer between 4-45, when the synthetic oligomer is of formula Ib;
X is H, or substituted or unsubstituted acyl; Y is $NH_2$, OH, acylamino, or acyloxy; provided that:
i) at least one monomer or up to 40 monomers are according to formula IIa, IIb, or IIc:

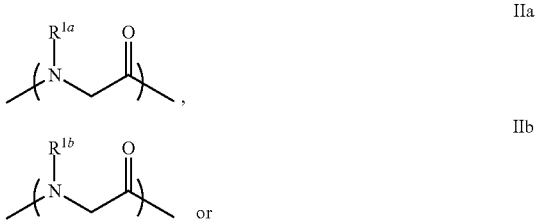

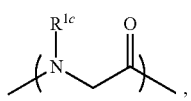

IIc wherein each $R^{1a}$ is independently unsubstituted alkyl, substituted alkyl, or cycloalkylalkyl;

each $R^{1b}$ is independently aminoalkyl, guanidinoalkyl ($H_2N$—$C$(=$NH$)—$NH$-alkyl), or N-containing heteroarylalkyl;

each $R^{1c}$ is independently substituted or unsubstituted aryl, substituted or unsubstituted aralkyl, substituted or unsubstituted heteroarylalkyl, or substituted or unsubstituted diarylalkyl; and ii) when $R^{1a}$ is Me; then the monomer adjacent to

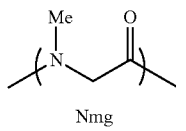

Nmg is other than

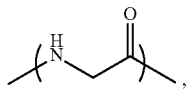
Gly (G)

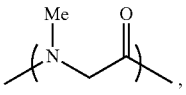
N-MeGly (Nmg)

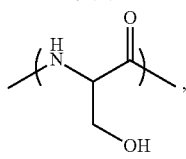
Ser (S)

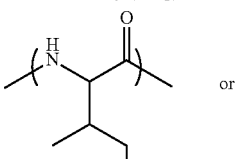 or
Ile (I)

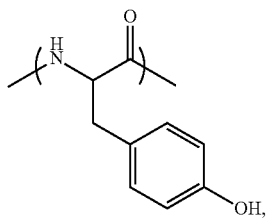
Tyr (Y)

or a salt thereof; and stereoisomers, isotopic variants and tautomers thereof.

In one embodiment, with respect to the compounds according to formula Ia or Ib, the synthetic oligomer is a β-strand forming peptide comprising of 42 amino acid residues, and wherein at least one or up to 35 amino acid residues are replaced independently with amino acid residues according to formula IIa, IIb, or IIc:

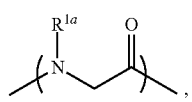
IIa

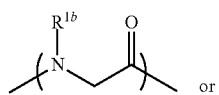
IIb
or

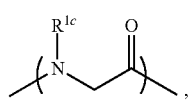
IIc wherein each $R^{1a}$ is independently unsubstituted alkyl, substituted alkyl, or cycloalkylalkyl;

each $R^{1b}$ is independently aminoalkyl, guanidinoalkyl ($H_2N$—$C$(=$NH$)—$NH$-alkyl), or N-containing heteroarylalkyl;

each $R^{1c}$ is independently substituted or unsubstituted aryl, substituted or unsubstituted aralkyl, substituted or unsubstituted heteroarylalkyl, or substituted or unsubstituted diarylalkyl;

X is H, or substituted or unsubstituted acyl; Y is $NH_2$, OH, acylamino, or acyloxy; or a salt thereof; and stereoisomers, isotopic variants and tautomers thereof.

In one embodiment, with respect to the compounds according to formula Ia or Ib, the synthetic oligomer is X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y (SEQ ID NO: 28);

Phe may be phenylalanine, or cyclohexylalanine;

and wherein at least one or up to 35 amino acid residues are replaced with amino acid residues independently selected from one or more Nap, Nab, Nah, Ngb, Npm, Nnm, Ndp, Nip, Mb, Nmg, and Nchm; and wherein:

| | |
|---|---|
| 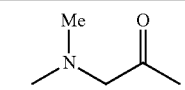 | Nmg = N-(methyl)glycine, |
| 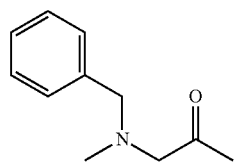 | Npm = N-(phenylmethyl)glycine, |
| 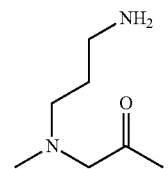 | Nap = N-(3-aminopropyl)glycine, |

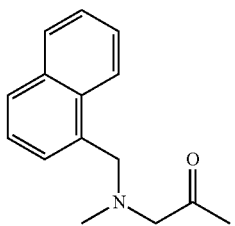 [SMILES: CC(=O)CN(C)Cc1cccc2ccccc12]
Nnm = N-(naphthylmethyl)glycine,

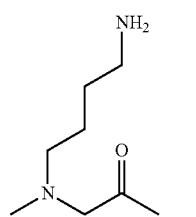
Nab = N-(4-aminobutyl)glycine

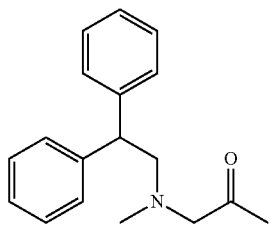 [SMILES: CC(=O)CN(C)CC(c1ccccc1)c1ccccc1]
Ndp = N-(2,2-diphenylethyl)glycine,

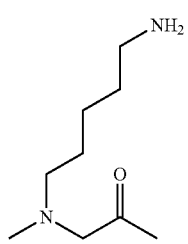
Nah = N-(6-aminohexyl)glycine

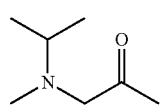
Nip = N-isopropyl)glycine,

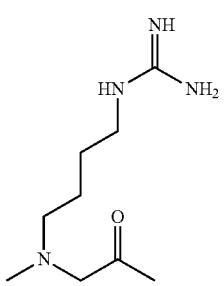
Ngb = N-(4-guanidinobutyl)glycine

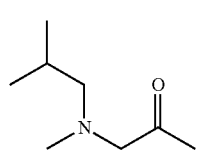
Nib = N-(isobutyl)glycine; and

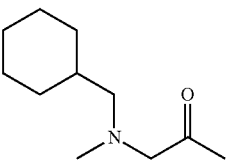
Nchm = N-(cyclohexylmethyl)glycine provided that none of -Gly-residues is replaced with Nmg.

In one particular embodiment, with respect to the compounds according to formula Ia or Ib, the synthetic oligomer is according to formula IIIa (SEQ ID NO: 36, wherein head-to-tail cyclization is absent), IIIb (SEQ ID NO: 36, wherein head-to-tail cyclization is present), IIIc (SEQ ID NO: 37, wherein head-to-tail cyclization is absent), IIId (SEQ ID NO: 37, wherein head-to-tail cyclization is present), IIIe (SEQ ID NO: 38, wherein head-to-tail cyclization is absent) or IIIf SEQ ID NO: 38, wherein head-to-tail cyclization is present):

$$X-[GKLVFFA]_t-Y,\quad \text{IIIa}$$

$$\boxed{[GKLVFFA]_t},\quad \text{IIIb}$$

$$X-[KLVFFA]_t-Y,\quad \text{IIIc}$$

$$\boxed{[KLVFFA]_t},\quad \text{IIId}$$

$$X-[QLVFFA]_t-Y,\text{ or}\quad \text{IIIe}$$

$$\boxed{[QLVFFA]_t},\quad \text{IIIf}$$

wherein

G, Q, K, L, V, F, and A are corresponding amino acid residues;

t is an integer between 1-5;

at least one or up to 3 of K, Q, L, V, F, and A are replaced with amino acid residues independently selected from one or more Nap, Nab, Nah, Ngb, Npm, Nnm, Ndp, Nip, Nib, Nmg, and Nchm;

X is H, or substituted or unsubstituted acyl; and Y is NH$_2$, OH, acylamino, or acyloxy;

provided that when the synthetic oligomer is according to formula IIIa, and when the K residue is replaced with the amino acid residue; then the K residue is replaced with residue other than Nmg;

or a salt thereof; and stereoisomers, isotopic variants and tautomers thereof.

In one particular embodiment, with respect to the compounds according to formula Ma, the K residue is replaced with amino acid residues independently selected from one or more Nap, Nab, Nah, Ngb, Npm, Nnm, Ndp, Nip, Nib, and Nchm.

In a further aspect, the present invention provides a method for the preparation of the peptoid or synthetic oligomers of the invention.

In one particular embodiment, with respect to the compounds of the invention, the compound is GKLVFNmgA (SEQ ID NO: 3).

In a further aspect, the peptoid or synthetic oligomers of the invention may be used to treat AD or other forms of dementia characterized by the presence of Aβ oligomers. The peptoid or synthetic oligomers could be designed and assembled to include the peptoid or synthetic oligomers pertinent for the treatment of AD, and then formulated into appropriate compositions and dosage forms for administration or application to an affected host. Moreover, such compositions may comprise a plurality of different peptoid or synthetic oligomers of the invention. Such compositions may further comprise mixtures or combinations of other therapeutic agents useful for the treatment of AD. In such formulations, the peptoid or synthetic oligomers of the invention may act synergistically with each other or other therapeutic agents, so that the resulting composition demonstrates improved effectiveness.

In a further aspect, the present invention provides pharmaceutical compositions comprising a peptoid of the invention, and a pharmaceutical carrier, excipient or diluent. In this aspect of the invention, the pharmaceutical composition can comprise one or more variant peptoid or synthetic oligomers of the invention, prepared, for example, with a differing array of peptoid linkers, to afford a more comprehensive treatment for a subject with AD. Likewise, and as stated above, the pharmaceutical compositions may comprise one or more of the peptoid or synthetic oligomers of the invention, in combination with other therapeutic agents.

In a further aspect of the invention, a method is disclosed for treating mammals, including humans, as well as lower mammalian species, susceptible to or afflicted with a condition attributable to or resulting from Aβ oligomerization, which method comprises administering an effective amount of a pharmaceutical composition containing or comprising the peptoid or synthetic oligomers just described.

In addition to the methods of treatment set forth above, the present invention extends to the use of any of the compounds of the invention for the preparation of medicaments or as medicaments that may be administered for such treatments, as well as to such compounds for the treatments disclosed and specified.

The present invention also encompasses therapeutic compositions for the treatment of AD comprising any of the compounds of the invention, a substrate comprising any of the compounds of the invention, wherein such a compound or compounds are bound to or incorporated into the substrate, and a device comprising such a substrate. Such articles include, without limitation, a medical device for transient or long term delivery of a compound or compounds of the invention.

Also encompassed herein are methods for making substrates or devices comprising any of the compounds of the invention. The present invention further extends to the use of any of the compounds of the invention for the generation of substrates or devices.

In additional aspects, this invention provides methods for synthesizing the complexes of the invention, with representative synthetic protocols and pathways disclosed later on herein.

Other objects and advantages will become apparent to those skilled in the art from a consideration of the ensuing detailed description, which proceeds with reference to the following illustrative drawings.

BRIEF DESCRIPTION OF THE DRAWINGS

FIG. 3 shows a graphical depiction of results from a Thioflavin T aggregation assay. Shown is a strong inhibitory effect of 1 µM GKLVFNmgA (SEQ ID NO: 3) on the aggregation of 100 µM of Aβ1-40 (1:100 compound:Aβ ratio, p<0.001). The effect of the unmodified base sequence GKLVFFA (SEQ ID NO: 1) on Aβ1-40 aggregation could be demonstrated only for 100 µM concentration (1:1 compound: Aβ ratio). GKLVFNmgA (SEQ ID NO: 3) does not form fibrils itself at 100 µM concentration. *p<0.05, p<0.01, *p<0.001 (Bonferoni post-hoc test following repeated measure ANOVA).

FIG. 4 shows the results of an oligomerization assay. (A) Aβ1-40 [100 µM] was aggregated alone or with addition of GKLVFNmgA [SEQ ID NO: 3; 10 µM] in conditions promoting oligomer assembly. Samples were treated with glutaraldehyde prior to SDS gel electrophoresis to prevent disassociation of oligomers. A strong smear of AB oligomers is seen between 40 and 70 KDa (arrowheads) whereas in the sample treated with GKLVFNmgA the density of these proteins is significantly reduced. A dense band below 25 KDa marker reflects non-dissociated AB monomers. Samples of 100 µM monomeric Aβ1-40 and glutaraldehyde were run as controls (lanes 1 and 4, respectively). (B) Densitometric analysis demonstrated that GKLVFNmgA (SEQ ID NO: 3) treatment reduced the amount of AB oligomers by 61.3% (p<0.01).

FIG. 5. Panel I shows a photomicrograph (A) revealing accumulation of aggregated FITC [Fluorescein isothiocyanate] labeled Aβ1-40 (green) on the surface of 18 day in vivo (DIV) primary hippocampal neurons immunostained against the NR1 subunit of the NMDA receptor (red). (A') Enlarged photomicrograph of a dendrite showing preferential co-localization of AB aggregates with anti-NR1 immunostaining as indicated by white arrows. (B) Reduced accumulation of aggregated Aβ1-40 (green) on the surface of 18 DIV under treatment with GKLVFNmgA (SEQ ID NO: 3). Panel II shows loss of (A) NMDA receptor, (B) post-synaptic density protein 95 (PSD-95), which is structurally and physiologically associated with NMDA receptor, and (C) synaptophysin in primary hippocampal neurons exposed to AB and rescue effect in neurons treated with GKLVFNmgA (SEQ ID NO: 3). 18 DIV neurons were grown for 72 hr in a medium containing Aβ1-40 (10 µM) or Aβ1-40 (10 µM) and GKLVFNmgA (SEQ ID NO: 3; 5 µM). Neurons were immunostained with anti-NR1 subunit monoclonal antibody (red) and their nuclei were counterstained with DAPI (blue). Panel III shows quantification of (A) NMDA receptor, (B) PSD-95, and (C) synaptophysin positive densities. Exposure of 18 DIV primary hippocampal neurons to 10 µM Aβ40 oligomers resulted in down regulation of NR1 NMDA receptor subunit to 48.6% of the control, along with synaptophysin and PSD-95 positive densities to 45.3% and 50.2% of the control, respectively ($p<0.001$). Co-treatment with 5 µM GKLVFNmgA (SEQ ID NO: 3) significantly ameliorated loss of NR1, synaptophysin, and PSD-95 expression by altering their levels to 83%, 84.5% and 82.3% of the control values, respectively; ($p<0.001$). Treatment of neurons with GKLVFNmgA (SEQ ID NO: 3) alone had no significant effect on the expression of these three synaptic proteins. ANOVA $p<0.0001$, values of Tukey's post hoc test indicated in the figure.

FIG. 8 shows (A) positioning of a microdialysis probe in the CA1 sector of the hippocampus of an Alzheimer's transgenic mouse. CA1 microdialysis is performed in awake, freely moving mice. This method is used to assess the concentration of soluble AB in brain interstitial fluid (ISF) that is exchangeable across a 38 kDa microdialysis membrane (eA$\beta_{1-x}$). eAβ pool includes monomeric Aβ as well as its dimers and trimers, but not Aβ coupled to apolipoproteins or large oligomers. (B) Shown is an effect of GKLVFNmgA (SEQ ID NO: 3) on brain interstitial fluid (ISF) eAβ in 9-month old APP$_{SW}$/PS1$_{L166P}$ AD transgenic mice (n=4). Delivery of 100 µM GKLVFNmgA (SEQ ID NO: 3) through reverse microdialysis into the CA1 area of the hippocampus resulted in substantial increases in the concentration of eA$\beta_{1-x}$ in the dialysate. The increase in eAβ concentration was observed from the seventh hour after the infusion onset and attained a maximal effect between hours 9 and 16 of the infusion, ranging between 250 and 300% of the basal ISF value. The striking effect of GKLVFNmgA (SEQ ID NO: 3) on ISF A$\beta_{1-x}$ confirms its anti-aggregation properties in vivo.

DETAILED DESCRIPTION OF THE INVENTION

Figure 1:
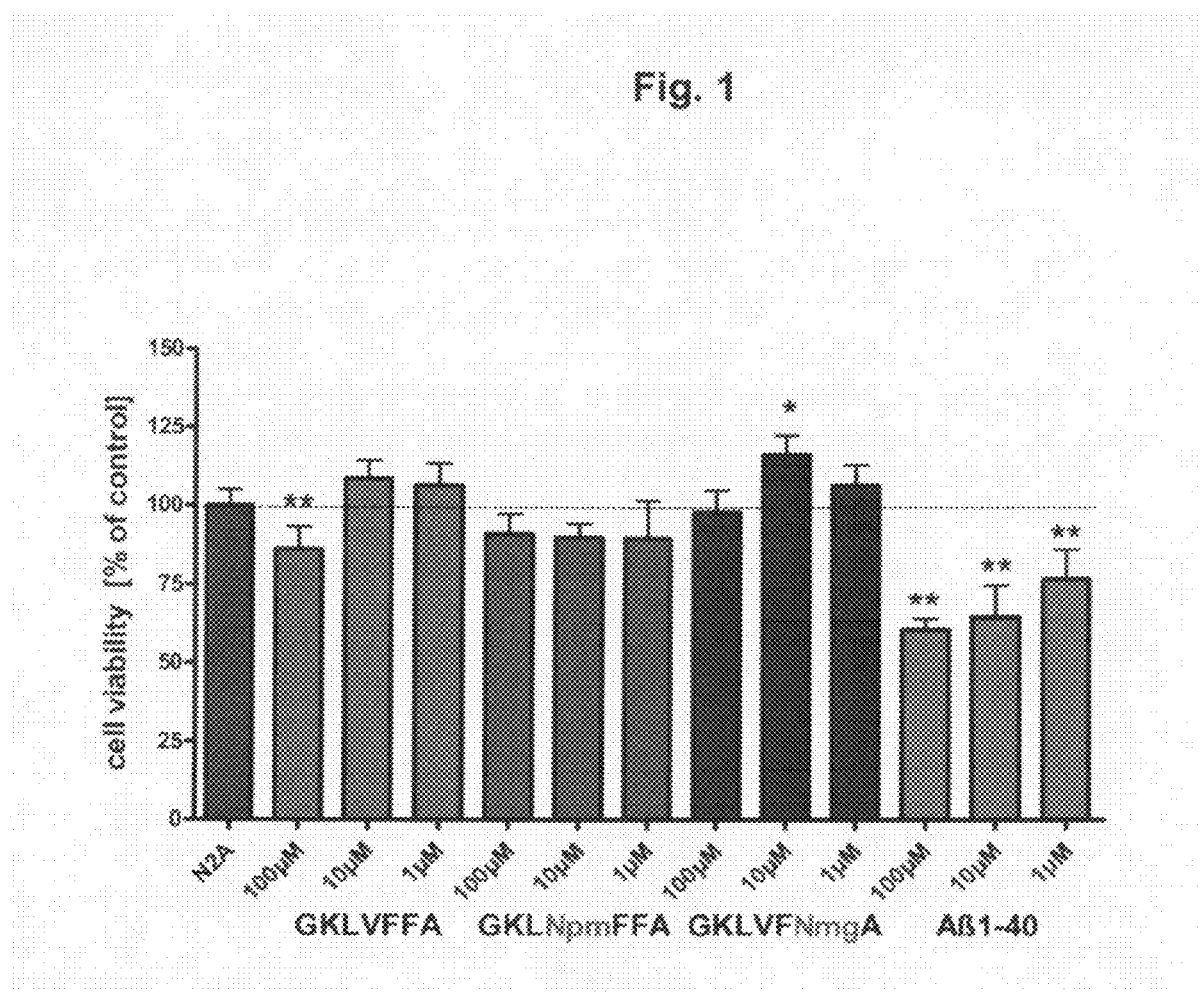
FIG. 1 shows a histogram bar graph depicting results from MTT [(3-(4,5-Dimethylthiazol-2-yl)-2,5-diphenyltetrazolium bromide] toxicity assay. Four day MTT cytotoxicity assay was conducted on SK-N-SH human neuroblastoma cells. Peptide/peptoid hybrids GKLNpmFFA (SEQ ID NO: 2) and GKLVFNmgA (SEQ ID NO: 3) showed no toxicity. Aβ16-21 (GKLVFFA; SEQ ID NO: 1) exhibited toxicity at the concentration of 100 µM whereas Aβ1-40 was toxic at the concentration of 1 µM. ANOVA p<0.0001; Dunett post hoc test *p<0.05, **p<0.01.

Alzheimer's disease (AD) is a neurodegenerative disease that causes dementia in millions of patients worldwide, for which no effective treatment is currently available. AD is a result of chronic and vast accumulation of a toxic and insoluble β-amyloid peptide (Aβ) peptide in the brain, which subsequently drives loss of synapses, triggers the occurrence of neurofibrillary pathology and neuroinflammation, and directly or indirectly causes neuronal loss (Hardy and Selkoe, 2002. Science; 297, 353-6; Tanzi et al. 2004, Neuron; 43, 605-8). Aβ is a hydrophobic peptide, prone to self-aggregation, encompassing 40 or 42 amino acids, which is derived from a cleavage of the larger, synaptic transmembrane protein, the amyloid precursor protein (APP) (Kang et al., 1987. Nature; 325, 733-6). Early-onset, familial AD cases harbor mutations in the APP sequence or mutations in presenilins (PS) 1 and 2, which either results in increased Aβ secretion or an increased production of more toxic and aggregation prone Aβ 1-42 form at the expense of more soluble Aβ1-40 (Duff et al. 996. Nature; 383, 710-3; Querfurth and LaFerla. 2010. N. Engl. J Med; 362, 329-44). In Down's syndrome subjects, an additional copy of the APP gene located on chromosome 21 also gives rise to increased Aβ production (Wisniewski et al. 1994. Dev. Brain Dysfunct. 7, 330-9). Reasons for Aβ accumulation in the more prevalent sporadic AD are less conspicuous, but they are believed to be a combination of inherited predispositions and acquired factors resulting in, progressing with age, a mismatch between production and clearance of Aβ (Querfurth and LaFerla. 2010. N. Engl. J Med; 362, 329-44; Tanzi et al. 2004, Neuron; 43, 605-8). Accumulation of Aβ in the brain is driven by its inherently low solubility and natural propensity to self-aggregate into toxic oligomers and insoluble fibrils (Lansbury et al., 1995. Nature Struct. Biol. 2, 990-8). Aβ oligomers appear to exert their toxic effect by binding to specific receptor protein and causing their down regulation. In particular, they bind and down regulate NMDA receptors on hippocampal pyramidal neurons, which are critical for synaptic plasticity and memory formation (Gong et al., 2003. Proc. Natl. Acad. Sci. USA; 100, 10417-22; Lacor et al., 2004. J Neurosci. 24, 10191-200; Lacor et al., 2007. J Neurosci. 27, 796-807). Furthermore, Aβ oligomers bind to lipid rich membrane rafts causing disruption of membrane integrity and may accumulate inside neuronal organelles resulting in dysfunction of mitochondria and endocytic/lysosomal pathway (Takuma et al., 2009. Proc. Natl. Acad. Sci. U.S.A; 106, 20021-6). In turn Aβ fibrils form Aβ plaques which are associated with deleterious activation of microglia and dystrophy of neurites in their vicinity (Meyer-Luehmann et al., 2008. Nature; 451, 720-4). Furthermore, self-aggregation of Aβ impacts its clearance as most of the mechanisms responsible for transporting Aβ outside the brain or degrading it in situ favor Aβ monomers. Aβ fibrils within plaques strongly attract Aβ monomers, so the occurrence of Aβ plaques in brain parenchyma is associated with doubling the half-life of soluble Aβ (Cirrito et al., 2003. J. Neurosci. 23, 8844-53), which in turn further perpetuates oligomerization and fibrillization. Therefore, an agent targeting self-assembly of Aβ into oligomers and fibrils would provide instant amelioration of synaptic toxicity, improve Aβ clearance limiting its accumulation in the brain, and prevent downstream neurodegenerative cascade caused by Aβ.

To date, there are no therapeutics effectively targeting build up of Aβ in the brain of Alzheimer's disease patients. Likewise, there are no therapeutics effectively targeting toxicity of Aβ oligomers which affects synaptic transmission, and in particular cause the dysfunction of NMDA receptors, which are critical for memory and learning. As described herein, the present inventors sought to develop therapeutic compounds capable of preventing aggregation of Aβ into toxic Aβ oligomers and fibrils, ameliorating intraneuronal build-up of Aβ, and ameliorating down regulation of synaptic proteins caused by Aβ oligomers. Results presented herein demonstrate that therapeutic agents with anti-Aβ oligomeric properties may be used to advantage to improve NMDA receptor signaling.

Pathogenesis of AD is associated with a massive accumulation of Aβ in the brain, which is driven by inherent hydrophobicity of Aβ and its natural propensity to self-aggregate into toxic oligomers and fibers. Transgenic (Tg) mice overexpressing human amyloid precursor protein mutant alone or together with a mutant of human presenilin 1 model early AD pathology and demonstrate profound memory impairment, which correlates with the presence of Aβ oligomers in the brain, but precedes timing of Aβ plaque formation. Furthermore, brain derived and synthetic Aβ oligomers were shown to impair hippocampal long-term potentiation, which is a physiological phenomenon underlying synaptic plasticity in the hippocampus and memory formation.

As indicated above, no effective treatment for Alzheimer's disease presently exists. Multiple lines of evidence indicate that pathogenesis of sporadic AD is associated with age-related accumulation of AB in the brain which triggers a neurodegenerative cascade leading to progressive synaptic dysfunction, neuronal loss, and symptoms of dementia. As described herein, the present inventors sought to generate peptidomimetic oligomers, which prevent aggregation of AB into toxic oligomers and fibrils, ameliorate intraneuronal build-up of Aβ, and ameliorate down regulation of synaptic proteins caused by AB oligomers. See, for example, Zuckermann et al. Current Opinion in Molecular Therapeutics 11: 299-307 (2009); and Ovadia et al. Bioorganic & Medicinal Chemistry 18:580-589 (2010) for additional information pertaining to the preparation and use of peptoids (peptidomimetic oligomers) as therapeutics, the entire contents of which are incorporated herein by reference. Replacement of amino acids with peptoid residues increases compound bioavailability since peptoid monomers are linked with an imide bond which is resistant to proteolytic degradation and the absence of hydrogen in amide groups therein reduces compound polarity, which improves cell membrane permeability. See, for example, Tan et al. Bioorganic & Medicinal Chemistry 16(11): 5853-5861, 2008. Furthermore, as shown herein, use of peptoids (e.g., GKLVFNmgA; SEQ ID NO: 3), rather than peptides, prevents toxicity resulting from β-sheet formation and may even provide additional β-sheet breaking properties.

In light of the results presented herein, the peptoids and compositions comprising same may be used to advantage in the prevention and/or treatment of AD. In a particular embodiment, the peptoids and compositions described herein are administered to a patient with early stage AD, prior to the onset of profound cognitive dysfunction. In a more particular embodiment, peptoids and compositions described herein are administered to a patient wherein early signs of AD are detected histologically or on the basis of imaging techniques that visualize pathology on a cellular and/or histological level (e.g., formation of Aβ fibrils and/or Aβ plaques) in the brain, which are characteristic of AD. Imaging techniques that can be used for detection directed to this purpose include, but are not limited to, positron emission tomography (PET), MRI (magnetic resonance imaging) and SPECT (single photon emission computerized tomography). In keeping with the results presented herein, peptoids and compositions described herein are administered to a patient with early stage AD, wherein mild cognitive dysfunction is evident. Ideally, the peptoids and compositions described herein are administered to a patient at early stages of AD, so as to maximize the therapeutic and preventative benefits of the peptoids and compositions administered to the patient.

DEFINITIONS

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

N-Substituted Glycine Monomer Designators:

Nap=N-(3-aminopropyl)glycine

Nab=N-(4-aminobutyl)glycine

Nah=N-(6-aminohexyl)glycine

Ngb=N-(4-guanidinobutyl)glycine

Npm=N-(phenylmethyl)glycine

Nnm=N-(naphthylmethyl)glycine

Ndp=N-(2,2-diphenylethyl)glycine

Nip=N-(isopropyl)glycine

Nib=N-(isobutyl)glycine

N-Substituted Glycine Monomer Designators:

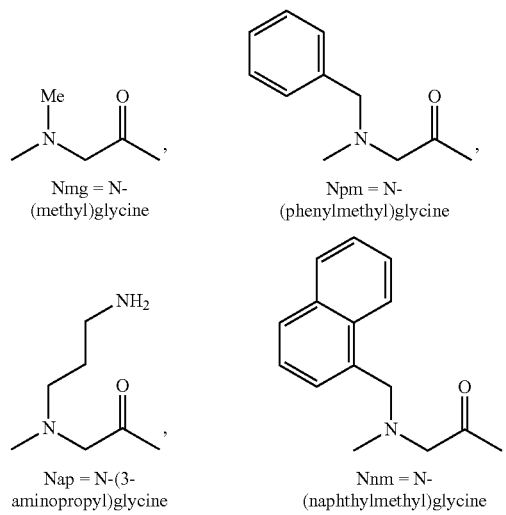

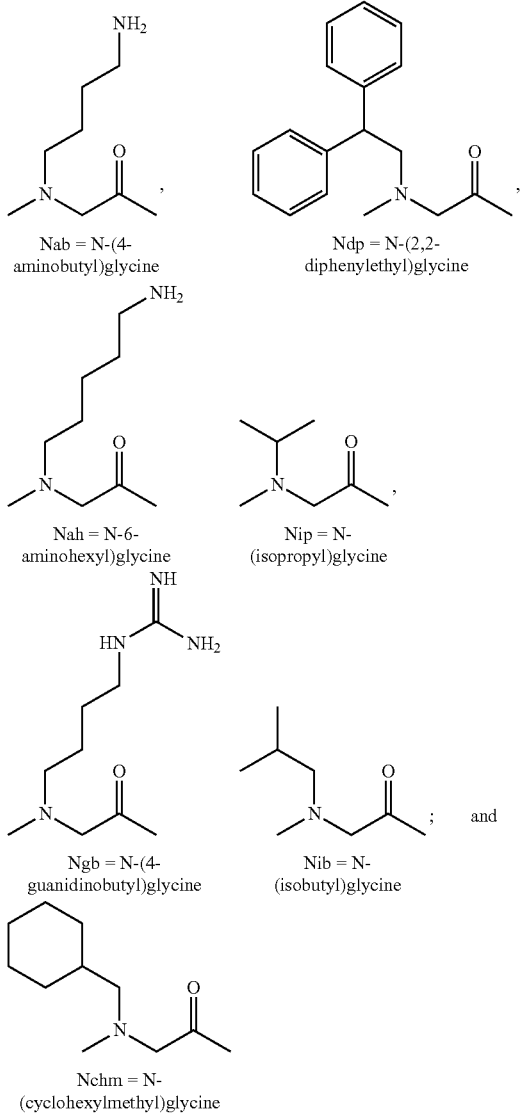

'Acyl' or 'Alkanoyl' refers to a radical —C(O)R$^{20}$, where R$^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
$C_1$-$C_8$ alkyl, substituted with halo or hydroxy; or
$C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —OR$^{29}$ where R$^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl, n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'"SO$_2$R", —SO$_2$NR"R"', —C(O)R", —C(O)OR", —OC(O)R", —NR'"C(O)R", —C(O)NR'R"', —NR"R'", or —(CR'"R"")$_m$OR'"; wherein each R" is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl; heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R'" and R"" independently represents H or $C_1$-$C_8$ alkyl.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

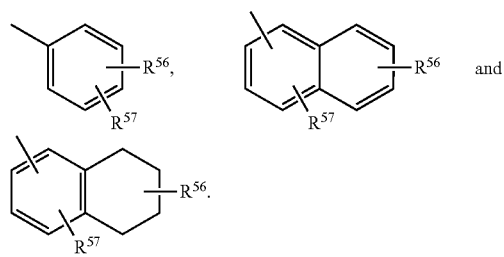

In these formulae one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocycloalkyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O or S. $R^{60}$ and $R^{61}$ are independently hydrogen, C1-C8 alkyl, C1-C4 haloalkyl, C3-C10 cycloalkyl, 4-10 membered heterocycloalkyl, C6-C10 aryl, substituted aryl, 5-10 membered heteroaryl.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

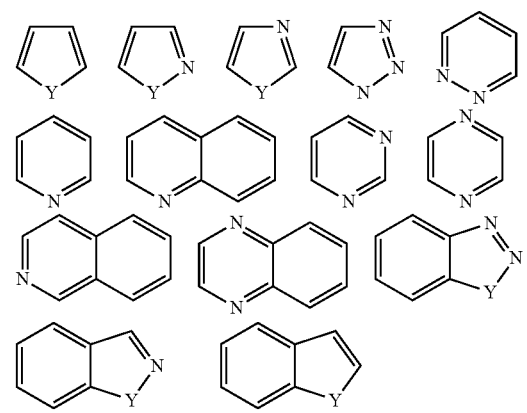

wherein each Y is selected from carbonyl, N, NR$^{65}$, O and S; and R$^{65}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

Examples of representative aryl having hetero atoms containing substitution include the following:

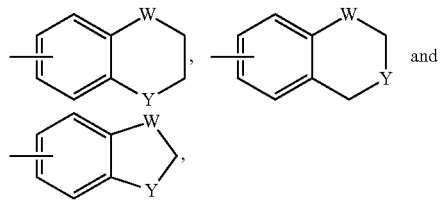

wherein each W is selected from C(R$^{66}$)$_2$, NR$^{66}$, O and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

"Unnatural amino acids" means amino acids and corresponding peptoid or synthetic oligomers that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989).

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject not yet exposed to or predisposed to the disease, and not yet experiencing or displaying symptoms of the disease).

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "patient" and "subject" are used interchangeably herein. Accordingly, a subject can be a mammal, in a particular embodiment a human. In other particular embodiments, a subject can be a bird, a reptile, an amphibian, or a plant.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

"Compound" refers to the synthetic oligomers of the invention. The terms "compounds" and "synthetic oligomers" means the same and are interchangeable.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the C$_1$ to C$_8$ alkyl, C$_2$-C$_8$ alkenyl, aryl, C$_7$-C$_{12}$ substituted aryl, and C$_7$-C$_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2$H or D), carbon-13 ($^{13}$C), nitrogen-15 ($^{15}$N), or the like. It will be understood that, in a compound comprising an unnatural proportion of an isotope, any example of an atom where present, may vary in isotope composition. For example, any hydrogen may be $^2$H/D, or any carbon may be $^{13}$C, or any nitrogen may be $^{15}$N, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in spade are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Peptoid of Synthetic Oligomers

As set forth earlier herein, the peptide/peptoid oligomers (peptidomimetic oligomers) of the present invention possess a variety of activities, including the ability to inhibit Aβ fibrillization and oligomerization, prevent loss of glutaminergic receptors, and ameliorate intraneuronal Aβ accumulation. Accordingly, the peptide/peptoid oligomers may be useful therapeutic agents for the treatment of diseases or disorders associated with Aβ fibrillization and oligomerization, such as AD. More particularly, the peptide/peptoid oligomers correspond to Aβ1-2 or fragments thereof. These peptide/peptoid oligomers can accordingly also include non-natural amino acids: beta-amino acids, D-amino acids and/or non-indigenous amino acids.

Figure 7:
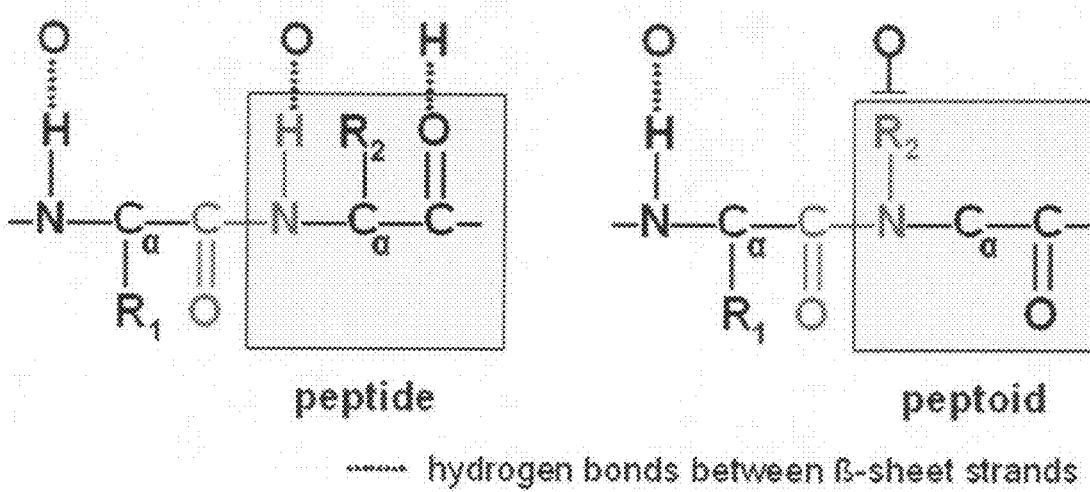
FIG. 7 depicts structural characteristics of peptoids and peptides. Peptoids are N-substituted glycine units where side chains mimicking groups of amino acids arise from amide nitrogen. In effect a peptide bond is replaced with an imide bond which is resistant to proteolytic degradation. Lack of hydrogen arising from the amide group reduces compound polarity and increases its lipid solubility, hence it may positively affect blood brain barrier permeability and, at the same time, abrogate formation of hydrogen bonds that facilitate β-sheet formation.

Peptoids exhibit many advantageous characteristics for development of bioactive compounds, as they are amenable to efficient solid phase synthesis; can incorporate highly diverse chemical functionalities; can establish a relationship between oligomer sequence, three-dimensional structure, and function; do not require the presence of chiral centers; can demonstrate marked resistance to degradation; and have superior cell permeability characteristics relative to peptides. See also FIG. 7, which depicts structural characteristics of peptoids and peptides.

More particularly, the present invention relates to peptide/peptoid oligomers or synthetic oligomer having anti-fibrillization and anti-oligomerization properties, according to formula Ia or Ib:

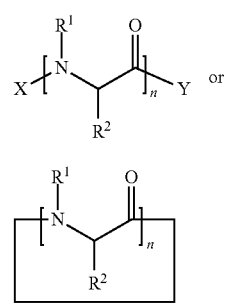

wherein
each $R^1$ is independently H, substituted or unsubstituted alkyl, substituted or unsubstituted cycloalkyl, substituted or unsubstituted aralkyl, substituted or unsubstituted cycloalkylalkyl, substituted or unsubstituted aryl, or substituted or unsubstituted heteroaryl;
each $R^2$ is independently hydrogen, or substituted or unsubstituted alkyl;
n is an integer between 2-45, when the synthetic oligomer is of formula Ia; and n is an integer between 4-45, when the synthetic oligomer is of formula Ib;
X is H, or substituted or unsubstituted acyl; Y is $NH_2$, OH, acylamino, or acyloxy; provided that:
i) at least one monomer or up to 40 monomers are according to formula IIa, IIb, or IIc:

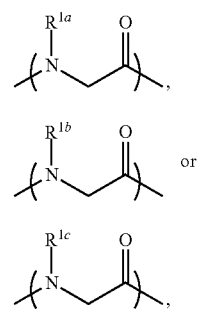

wherein
each $R^{1a}$ is independently unsubstituted alkyl, substituted alkyl, or cycloalkylalkyl;
each $R^{1b}$ is independently aminoalkyl, guanidinoalkyl ($H_2N$—C(=NH)—NH-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalkyl; and
ii) when $R^{1a}$ is Me; then the monomer adjacent to

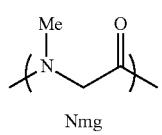

Nmg is other than

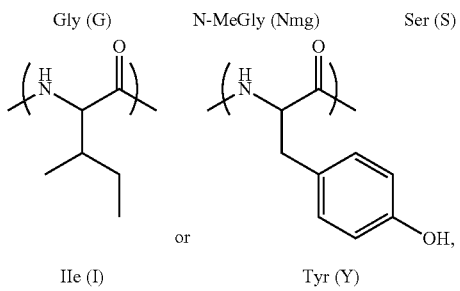

Gly (G)   N-MeGly (Nmg)   Ser (S)

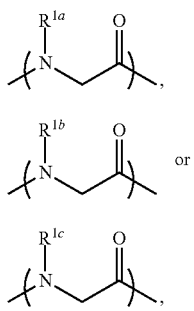

Ile (I)   Tyr (Y)

or a salt thereof; and stereoisomers, isotopic variants and tautomers thereof.

In one embodiment, with respect to the compounds according to formula Ia or Ib, the synthetic oligomer is a β-strand forming peptide comprising of 42 amino acid residues, and wherein
at least one or up to 35 amino acid residues are replaced independently with amino acid residues according to formula IIa, IIb, or IIc:

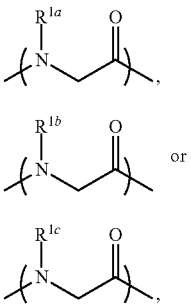

wherein
each $R^{1a}$ is independently unsubstituted alkyl, substituted alkyl, or cycloalkylalkyl;
each $R^{1b}$ is independently aminoalkyl, guanidinoalkyl ($H_2N-C(=NH)-NH$-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalkyl;
X is H, or substituted or unsubstituted acyl; Y is $NH_2$, OH, acylamino, or acyloxy; or a salt thereof; and stereoisomers, isotopic variants and tautomers thereof.

The synthetic oligomer according to claim 2, wherein the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y (SEQ ID NO: 28);

Phe may be phenylalanine, or cyclohexylalanine;
and wherein at least one or up to 35 amino acid residues are replaced independently with amino acid residues according to formula IIa, IIb, or IIc:

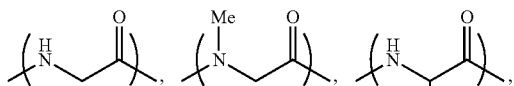

wherein
each $R^{1a}$ is independently unsubstituted alkyl, substituted alkyl, or cycloalkylalkyl;
each $R^{1b}$ is independently aminoalkyl, guanidinoalkyl ($H_2N-C(=NH)-NH$-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalkyl;
provided that when the amino acid residue -Gly- is replaced with the amino acid residue according to formula IIa, then $R^{1a}$ is other than Me.

In one embodiment, with respect to the compounds according to formula Ia or Ib, the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y (SEQ ID NO: 28);

Phe may be phenylalanine, or cyclohexylalanine;
and wherein at least one or up to 35 amino acid residues are replaced with amino acid residues independently selected from one or more Nap, Nab, Nah, Ngb, Npm, Nnm, Ndp, Nip, Nib, Nmg, and Nchm; and
wherein:

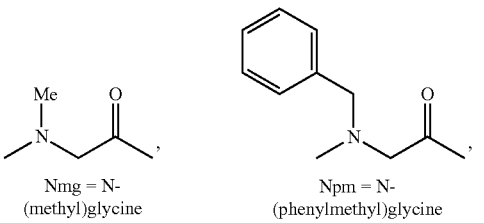

Nmg = N-(methyl)glycine    Npm = N-(phenylmethyl)glycine

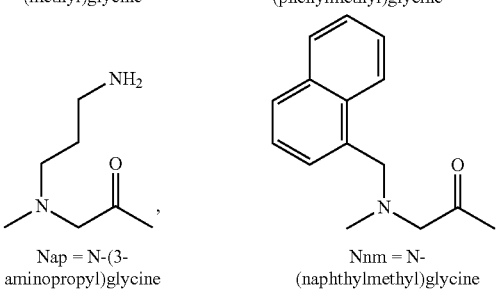

Nap = N-(3-aminopropyl)glycine    Nnm = N-(naphthylmethyl)glycine

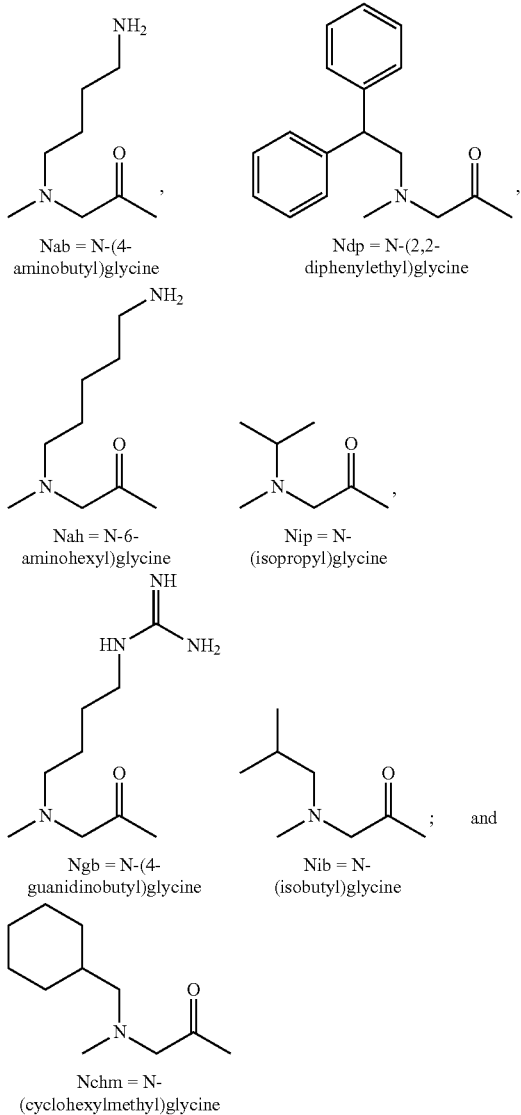

Nab = N-(4-aminobutyl)glycine

Ndp = N-(2,2-diphenylethyl)glycine

Nah = N-6-aminohexyl)glycine

Nip = N-(isopropyl)glycine

Ngb = N-(4-guanidinobutyl)glycine

Nib = N-(isobutyl)glycine

Nchm = N-(cyclohexylmethyl)glycine provided that none of -Gly-residues is replaced with Nmg.

In one embodiment, with respect to the compounds according to formula Ia or Ib, the synthetic oligomer comprises-His-His-Gln-Lys-Leu-Val-Phe-Phe-Ala- (SEQ ID NO: 29); and wherein at least one or up to 5 amino acid residues of -His-His-Gln-Lys-Leu-Val-Phe-Phe-Ala- (SEQ ID NO: 29) are replaced with amino acid residues independently selected from one or more Nap, Nab, Nah, Ngb, Npm, Nnm, Ndp, Nip, Mb, Nmg, and Nchm. In one particular embodiment at least one or up to 5 amino acid residues of -His-His-Gln-Lys-Leu-Val-Phe-Phe-Ala- (SEQ ID NO: 29) are replaced with Nmg.

In another embodiment, with respect to the compounds according to formula Ia or Ib, the synthetic oligomer comprises-Gln-Lys-Leu-Val-Phe-Phe-Ala- (SEQ ID NO: 30); and wherein at least one or up to 4 amino acid residues of -Gln-Lys-Leu-Val-Phe-Phe-Ala- (SEQ ID NO: 30) are replaced with amino acid residues independently selected from one or more Nap, Nab, Nah, Ngb, Npm, Nnm, Ndp, Nip, Nib, Nmg, and Nchm. In one particular embodiment at least one or up to 4 amino acid residues of -Gln-Lys-Leu-Val-Phe-Phe-Ala- (SEQ ID NO: 30) are replaced with Nmg.

In another embodiment, with respect to the compounds according to formula Ia or Ib, the synthetic oligomer comprises-Lys-Leu-Val-Phe-Phe-Ala- (SEQ ID NO: 4); and wherein at least one or up to 3 amino acid residues of -Lys-Leu-Val-Phe-Phe-Ala- (SEQ ID NO: 4) are replaced with amino acid residues independently selected from one or more Nap, Nab, Nah, Ngb, Npm, Nnm, Ndp, Nip, Nib, Nmg, and Nchm. In one particular embodiment at least one or up to 3 amino acid residues of -Lys-Leu-Val-Phe-Phe-Ala- (SEQ ID NO: 4) are replaced with Nmg.

In another embodiment, with respect to the compounds according to formula Ia or Ib, the synthetic oligomer comprises-Leu-Val-Phe-Phe-Ala- (SEQ ID NO: 31); and wherein at least one or up to 2 amino acid residues of -Leu-Val-Phe-Phe-Ala- (SEQ ID NO: 31) are replaced with amino acid residues independently selected from one or more Nap, Nab, Nah, Ngb, Npm, Nnm, Ndp, Nip, Nib, Nmg, and Nchm. In one particular embodiment at least one or up to 2 amino acid residues of -Leu-Val-Phe-Phe-Ala- (SEQ ID NO: 31) are replaced with Nmg.

In another embodiment, with respect to the compounds according to formula Ia or Ib, the synthetic oligomer comprises-Val-Phe-Phe-; and wherein at least one amino acid residue of -Val-Phe-Phe- is replaced independently with amino acid residues according to formula IIa, IIb, or IIc. In one particular embodiment at least one amino acid residue of -Val-Phe-Phe- is replaced with Nmg.

In one embodiment, with respect to the compounds according to formula Ia or Ib, the synthetic oligomer is X-Gly-Lys-Leu-Val-Phe-Phe-Ala-Glu-Asp-Val-Gly-Y (SEQ ID NO: 32); and wherein at least one or up to 5 amino acid residues are replaced independently with amino acid residues according to formula IIa, IIb, or IIc or with amino acid residues independently selected from one or more Nap, Nab, Nah, Ngb, Npm, Nnm, Ndp, Nip, Nib, Nmg, and Nchm. In one particular embodiment at least one or up to 5 amino acid residues of -Gly-Lys-Leu-Val-Phe-Phe-Ala-Glu-Asp-Val-Gly- (SEQ ID NO: 32) are replaced with Nmg.

In another embodiment, with respect to the compounds according to formula Ia or Ib, the synthetic oligomer is X-Gly-Lys-Leu-Val-Phe-Phe-Ala-Glu-Y (SEQ ID NO: 33); and wherein at least one or up to 4 amino acid residues are replaced independently with amino acid residues according to formula IIa, IIb, or IIc or with amino acid residues independently selected from one or more Nap, Nab, Nah, Ngb, Npm, Nnm, Ndp, Nip, Mb, Nmg, and Nchm. In one particular embodiment at least one or up to 4 amino acid residues of -Gly-Lys-Leu-Val-Phe-Phe-Ala-Glu- (SEQ ID NO: 33) are replaced with Nmg.

In one embodiment, with respect to the compounds according to formula Ia or Ib, the synthetic oligomer is X-Gly-Lys-Leu-Val-Phe-Phe-Y (SEQ ID NO: 34); and wherein at least one or up to 4 amino acid residues are replaced independently with amino acid residues according to formula IIa, IIb, or IIc or with amino acid residues independently selected from one or more Nap, Nab, Nah, Ngb, Npm, Nnm, Ndp, Nip, Nib, Nmg, and Nchm. In one particular embodiment at least one or up to 4 amino acid residues of -Gly-Lys-Leu-Val-Phe-Phe- (SEQ ID NO: 34) are replaced with Nmg.

In one particular embodiment, with respect to the compounds according to formula Ia or Ib, the synthetic oligomer is according to formula IIIa (SEQ ID NO: 36, wherein head-to-tail cyclization is absent), IIIb (SEQ ID NO: 36, wherein head-to-tail cyclization is present), IIIc (SEQ ID NO: 37, wherein head-to-tail cyclization is absent), IIId (SEQ ID NO: 37, wherein head-to-tail cyclization is present), Me (SEQ ID NO: 38, wherein head-to-tail cyclization is absent) or IIIf SEQ ID NO: 38, wherein head-to-tail cyclization is present):

 IIIa

 IIIb

 IIIc

 IIId

 IIIe

 IIIf wherein
wherein G, K, Q, L, V, and A are corresponding amino acid residues; and F is phenylalanine or cyclohexylalanine,
t is an integer between 1-5;
at least one or up to 3 of K, Q, L, V, F, and A are replaced with amino acid residues according to formula IIa, IIb, or IIc:

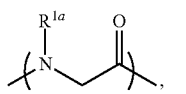 IIa

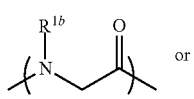 IIb

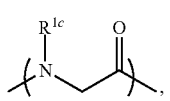 IIc wherein
each $R^{1a}$ is independently unsubstituted alkyl; substituted alkyl, or cycloalkylalkyl;
each $R^{1b}$ is independently aminoalkyl, guanidinoalkyl ($H_2N-C(=NH)-NH$-alkyl), or N-containing heteroarylalkyl;
each $R^{1c}$ is independently substituted or unsubstituted aryl, substituted or unsubstituted aralkyl, substituted or unsubstituted heteroarylalkyl, or substituted or unsubstituted diarylalkyl;
X is H, or substituted or unsubstituted acyl; Y is $NH_2$, OH, acylamino, or acyloxy;
provided that when the amino acid residue K is replaced with the amino acid residue according to formula IIa, then $R^{1a}$ is other than Me;
or a salt thereof; and stereoisomers, isotopic variants and tautomers thereof.

In another embodiment, with respect to the compounds according to formulae Ia-IIIb, the compound comprises the amino acid residue according to formula IIa, and $R^{1a}$ is Me, Et, n-Pr, Pr, n-Bu, sec-Bu, i-Bu, or cyclohexylmethyl.

In one embodiment, with respect to the compounds according to formulae Ia-IIIb, the compound comprises the amino acid residue according to formula IIc, and $R^{1c}$ is phenyl or benzyl, unsubstituted or substituted with one or more groups selected from alkyl, halo, hydroxy, amino, nitro, and alkoxy.

In another embodiment, with respect to the compounds according to formulae Ia-IIIb, the compound comprises the amino acid residue according to formula IIc, and $R^{1c}$ is phenethyl, unsubstituted or substituted with one or more groups selected from alkyl, halo, hydroxy, amino, nitro, and alkoxy.

In another embodiment, with respect to the compounds according to formulae Ia-IIIb, the compound comprises the amino acid residue according to formula IIc, and $R^{1c}$ is 2-naphthyl, unsubstituted or substituted with one or more groups selected from alkyl, halo, hydroxy, amino, nitro, and alkoxy.

In another embodiment, with respect to the compounds according to formulae Ia-IIIb, the compound comprises the amino acid residue according to formula IIc, and $R^{1c}$ is 2,2-diphenylethyl, unsubstituted or substituted with one or more groups selected from alkyl, halo, hydroxy, amino, nitro, and alkoxy.

In another embodiment, with respect to the compounds according to formulae Ia-IIIb, the compound comprises the amino acid residue according to formula IIc, and $R^{1c}$ is furanyl or thienyl, unsubstituted or substituted with one or more groups selected from alkyl, halo, hydroxy, amino, nitro, and alkoxy.

In one embodiment, with respect to the compounds according to formulae Ia-IIIb, the compound comprises the amino acid residue according to formula IIb, and $R^{1b}$ is aminomethyl, 2-aminoethyl, 3-aminopropyl, 4-aminobutyl, 5-aminopentyl, or 6-aminohexyl.

In another embodiment, with respect to the compounds according to formulae Ia-IIIb, the compound comprises the amino acid residue according to formula IIb, and $R^{1b}$ is 3-aminopropyl.

In one embodiment, with respect to the compounds according to formulae Ia-IIIb, the compound comprises the amino acid residue according to formula IIb, and $R^{1b}$ is guanidinoalkyl.

In another embodiment, with respect to the compounds according to formulae Ia-IIIb, the compound comprises the amino acid residue according to formula IIb, and $R^{1b}$ is guanidinomethyl, 2-guanidinoethyl, 3-guanidinopropyl, 4-guanidinobutyl, 5-guanidinopentyl, or 6-guanidinohexyl.

In another embodiment, with respect to the compounds according to formulae Ia-IIIb, the compound comprises the amino acid residue according to formula IIb, and $R^{1b}$ is 4-guanidinobutyl.

In another embodiment, with respect to the compounds according to formulae Ia-IIIb, the compound comprises the amino acid residue according to formula IIb, and $R^{1b}$ is imidazolylmethyl, 2-imidazolylethyl, 3-imidazolylpropyl, 4-imidazolylbutyl, 5-imidazolylpentyl, or 6-imidazolylhexyl.

In another embodiment, with respect to the compounds according to formulae Ia-IIIb, the compound comprises the amino acid residue according to formula IIb, and $R^{1b}$ is methyl, n-propyl, n-butyl, n-pentyl, and n-hexyl, substituted with pyrrolyl, oxazolyl, isoxazolyl, thiazolyl, thiadiazolyl, triazolyl, or tetrazolyl.

In one particular embodiment, with respect to the compounds according to formula Ia or Ib, the synthetic oligomer is according to formula IIIa (SEQ ID NO: 36, wherein head-to-tail cyclization is absent), IIIb (SEQ ID NO: 36, wherein head-to-tail cyclization is present), IIIc (SEQ ID NO: 37, wherein head-to-tail cyclization is absent), IIId (SEQ ID NO: 37, wherein head-to-tail cyclization is present), IIIe (SEQ ID NO: 38, wherein head-to-tail cyclization is absent) or IIIf (SEQ ID NO: 38, wherein head-to-tail cyclization is present):

 IIIa

 IIIb

 IIIc

 IIId

 IIIe

 IIIf wherein

G, K, Q, L, V, F, and A are corresponding amino acid residues;

t is an integer between 1-5;

at least one or up to 3 of K, Q, L, V, F, and A are replaced with amino acid residues independently selected from one or more Nap, Nab, Nah, Ngb, Npm, Nnm, Ndp, Nip, Nib, Nmg, and Nchm; and wherein:

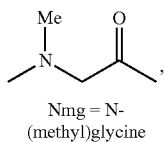
Nmg = N-(methyl)glycine

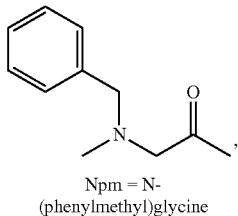
Npm = N-(phenylmethyl)glycine

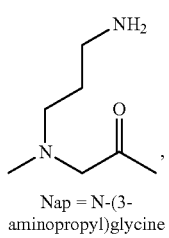
Nap = N-(3-aminopropyl)glycine

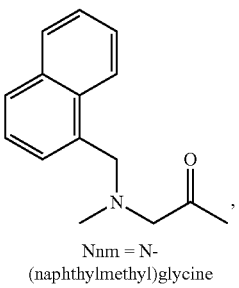
Nnm = N-(naphthylmethyl)glycine

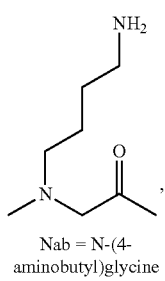
Nab = N-(4-aminobutyl)glycine

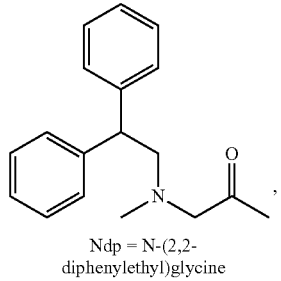
Ndp = N-(2,2-diphenylethyl)glycine

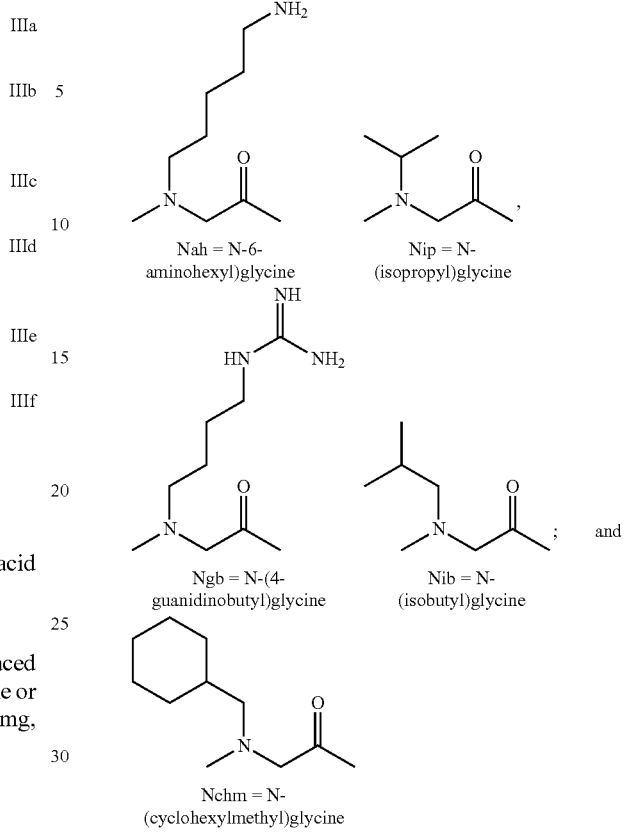

Nah = N-6-aminohexyl)glycine

Nip = N-(isopropyl)glycine

Ngb = N-(4-guanidinobutyl)glycine

Nib = N-(isobutyl)glycine

; and

Nchm = N-(cyclohexylmethyl)glycine

X is H, or substituted or unsubstituted acyl; and Y is NH$_2$, OH, acylamino, or acyloxy;

provided that when the synthetic oligomer is according to formula IIIa, and when the K residue is replaced with the amino acid residue; then the K residue is replaced with residue other than Nmg; or a salt thereof; and stereoisomers, isotopic variants and tautomers thereof.

In one embodiment, with respect to the compounds according to formula IIIa, the K residue is replaced with amino acid residues independently selected from one or more Nap, Nab, Nah, Ngb, Npm, Nnm, Ndp, Nip, Nib, and Nchm.

In one embodiment, with respect to the compounds according to formula IIIa, the K residue is replaced with amino acid residue independently selected from Nap, Nab, Nah, Ngb, Npm, Nnm, Ndp, Nip, Nib, and Nchm.

In one embodiment, with respect to the compounds according to formula IIIa, the compound is other than

wherein GNmgLVFFA corresponds to SEQ ID NO: 35.

In one embodiment, with respect to the compounds according to formulae Ia-IIIf, at least one of K, L, V, F, and A is replaced with N-phenylmethylglycine (Npm), N-cyclohexylmethylamine (Nchm), or N-methylglycine (Nmg); provided that the compound is other than X-[GNmgLVFFA]$_t$-Y (SEQ ID NO: 39).

In one embodiment, with respect to the compounds according to formulae at least one of Q, L, V, F, and A is replaced with N-phenylmethylglycine (Npm), N-cyclohexylmethylamine (Nchm), or N-methylglycine (Nmg).

In another embodiment, with respect to the compounds according to formulae one F is replaced with N-phenylmethylglycine (Npm), N-cyclohexylmethylamine (Nchm), or N-methylglycine (Nmg).

In another embodiment, with respect to the compounds according to formulae the synthetic oligomer is a linear peptoid according to formula Ia, IIIa, IIIc or IIIe.

In another embodiment, with respect to the compounds according to formulae the synthetic oligomer is a cyclic peptoid according to formula Ib, IIIb, III or IIIf.

In one embodiment, with respect to the compounds according to formulae the subscript t is 1, 2, 3, 4 or 5. In another embodiment t is 1, 2, or 3. In a particular embodiment t is 1.

In another embodiment, with respect to the compounds according to formulae Ia-IIIf, the synthetic oligomer is X-(GKLVFNpmA)$_t$-Y (SEQ ID NO: 40), X-(GKLVNpmFA)$_t$-Y (SEQ ID NO: 41), X-(GKLVFNchmA)$_t$-Y (SEQ ID NO: 42), X-(GKLVNchmFA)$_t$-Y (SEQ ID NO: 43), X-(GKLVFNmgA)$_t$-Y (SEQ ID NO: 44), or X-(GKLVNmgFA; SEQ ID NO: 23)$_t$-Y (SEQ ID NO: 45); and the subscript t is 1, 2, 3, 4 or 5. In another embodiment t is 1, 2, or 3. In a particular embodiment t is 1. The following sequences correspond to the indicated sequence identifiers: GKLVFNpmA (SEQ ID NO: 22); GKLVNpmFA (SEQ ID NO: 17); GKLVFNchmA (SEQ ID NO: 19); GKLVNchmFA (SEQ ID NO: 20); GKLVFNmgA (SEQ ID NO: 3); and GKLVNmgFA (SEQ ID NO: 23).

In one particular embodiment, with respect to the compounds according to formulae both Fs are replaced independently with N-phenylmethylglycine (Npm), N-cyclohexylmethylamine (Nchm), or N-methylglycine (Nmg).

In another particular embodiment, with respect to the compounds according to formulae Ia-IIIf, the synthetic oligomer is X-(GKLVNpmNpmA)$_t$-Y (SEQ ID NO: 46), X-(GKLVNchmNchmA)$_t$-Y (SEQ ID NO: 47), or X-(GKLVNmgNmgA)$_t$-Y (SEQ ID NO: 48); and the subscript t is 1, 2, 3, 4 or 5. In another embodiment t is 1, 2, or 3. In a particular embodiment t is 1. The following sequences correspond to the indicated sequence identifiers: GKLVNpmNpmA (SEQ ID NO: 18); GKLVNchmNchmA (SEQ ID NO: 21); and GKLVNmgNmgA (SEQ ID NO: 24).

In another particular embodiment, with respect to the compounds according to formulae Ia-IIIf, the synthetic oligomer is X-(GKLVFNmgA)$_t$-Y (SEQ ID NO: 44); and the subscript t is 1, 2, 3, 4 or 5. In another embodiment t is 1, 2, or 3. In a particular embodiment t is 1.

In one embodiment, with respect to the compounds according to formula Ia or Ib, the peptoid is according to formula IVa (SEQ ID NO: 22), IVb (SEQ ID NO: 17), or IVc (SEQ ID NO: 18):

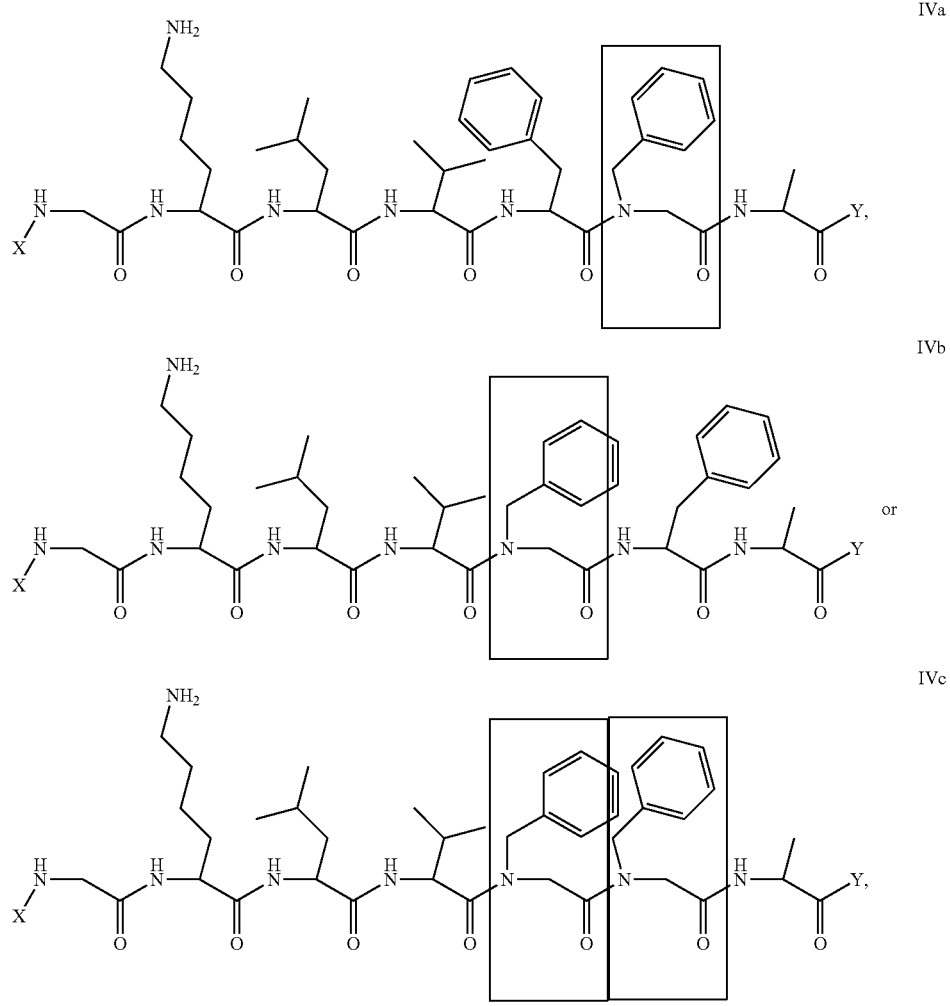

wherein X, and Y are as described for formula Ia or Ib.

In one embodiment, with respect to the compounds according to formula Ia or Ib, the synthetic oligomer is according to formula Va (SEQ ID NO: 3), Vb (SEQ ID NO: 23), or Vc (SEQ ID NO: 24):

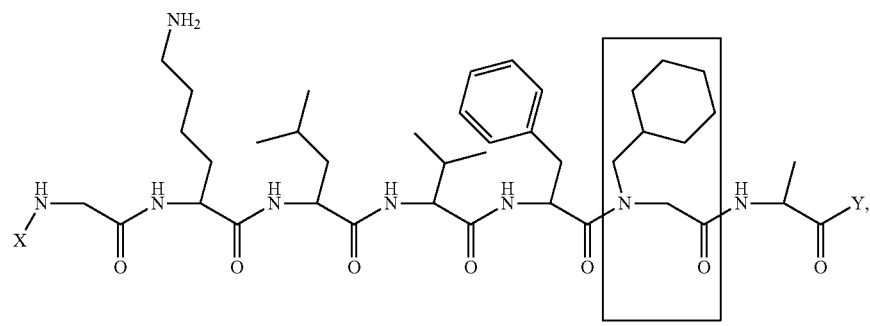

wherein X, and Y are as described for formula Ia or Ib.

In one embodiment, with respect to the compounds according to formula Ia or Ib, the synthetic oligomer is according to formula VIa (SEQ ID NO: 19), VIb (SEQ ID NO: 20), or VIc (SEQ ID NO: 21):

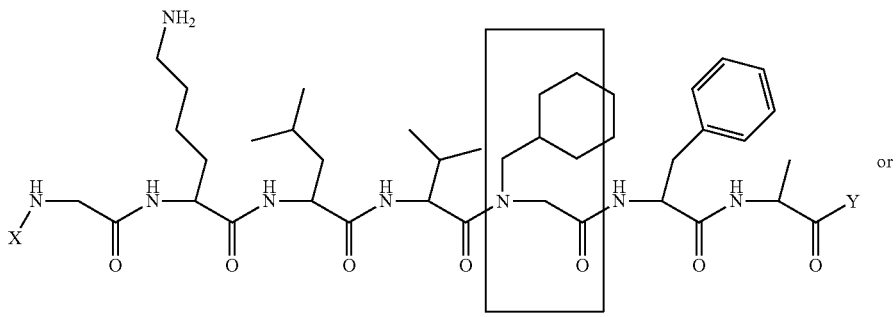

VIb

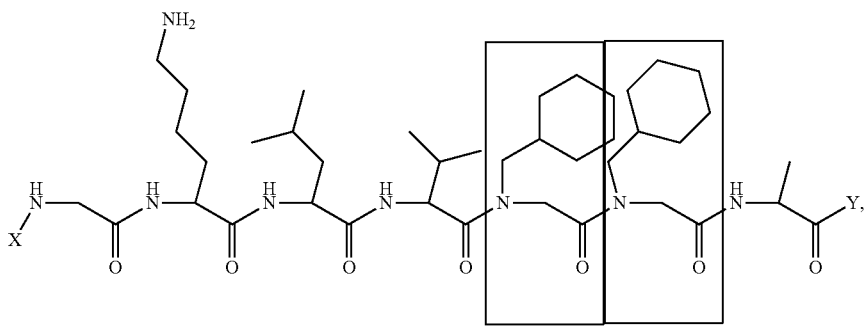

VIc wherein X, and Y are as described for formula Ia or Ib.

In one embodiment, with respect to the compounds according to formula Ia or Ib, the synthetic oligomer is according to formula VII:

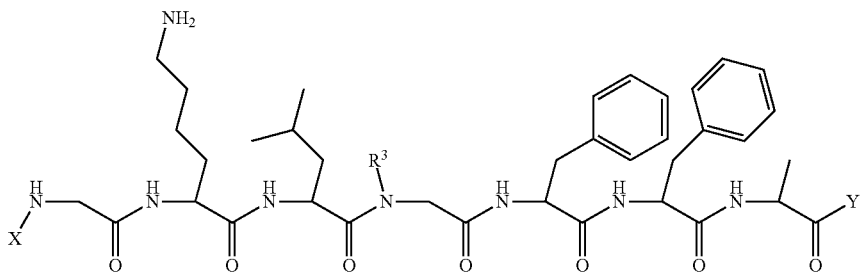

VII wherein X, and Y are as described for formula Ia or Ib; $R^3$ is Me (SEQ ID NO: 49), phenylmethyl (SEQ ID NO: 2), or cyclohexylmethyl (SEQ ID NO: 50).

In one embodiment, with respect to the compounds according to formula Ia or Ib, the synthetic oligomer is according to formula VIIIa (SEQ ID NO: 49) or VIIIb (SEQ ID NO: 2):

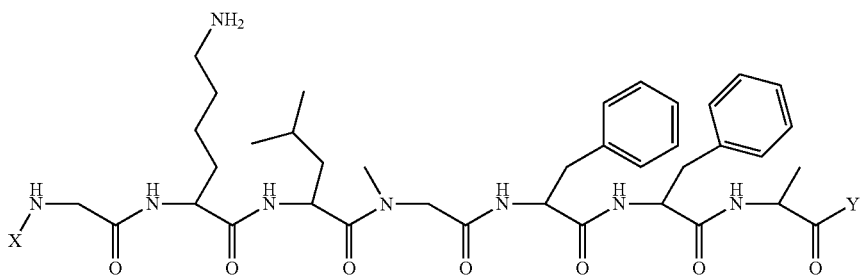

VIIIa

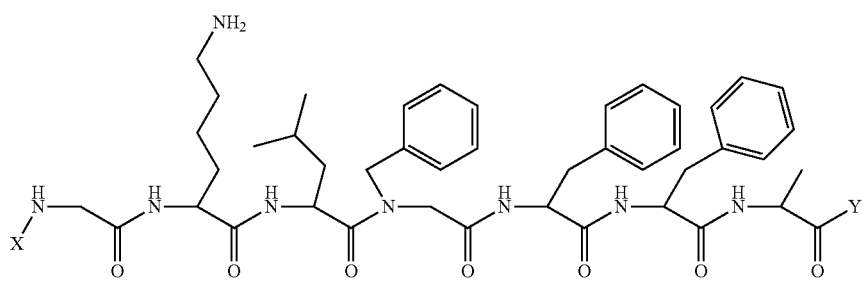

VIIIb wherein X, and Y are as described for formula Ia or Ib.

In one embodiment, with respect to the compounds according to formulae Ia-VIIIb, X is acetyl.

In one particular embodiment, with respect to the compounds according to formulae Ia-VIIIb, X is H.

In one embodiment, with respect to the compounds according to formulae Ia-VIIIb, Y is $NH_2$.

In one embodiment, with respect to the compounds according to formula Ia or Ib, the synthetic oligomer is according to formula IXa (SEQ ID NO: 3):

IXa

In one embodiment, with respect to the compounds according to formula Ia or Ib, the synthetic oligomer is according to formula IXb (SEQ ID NO: 3, wherein glycine at position 1 is attached to an acetyl group):

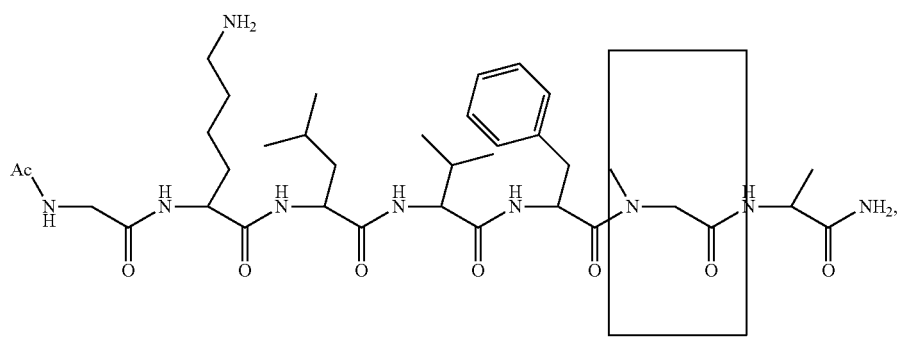

IXb

In one embodiment, 'acyl' refers to a radical —C(O)R$^{20}$, where R$^{20}$ is Me, Et, n-Pr, i-Pr, n-Bu, i-Bu, pentyl, hexyl, heptyl, octyl, nonyl, or decyl.

In one embodiment 'acyl' refers to a radical —C(O)R$^{20}$, where R$^{20}$ is C$_{11}$-C$_{20}$ alkyl.

In one particular embodiment, "acyl" is lauroyl, tridecanoyl, myristoyl, pentadecanoyl, palmitoyl, or cetoyl.

In one embodiment, 'acyl' refers to a radical —C(O)R$^{20}$, where R$^{20}$ is C$_3$-C$_{10}$ cycloalkyl. In another embodiment, R$^{20}$ is cyclopropyl, cyclobutyl, cyclopentyl or cyclohexyl.

In one embodiment, 'acyl' refers to a radical —C(O)R$^{20}$, where R$^{20}$ is —(CH$_2$)$_{t'}$(C$_3$-C$_{10}$ cycloalkyl), and t' is 1, 2, or 3. In another embodiment R$^{20}$ is —CH$_2$—(C$_3$-C$_{10}$ cycloalkyl). In yet another embodiment R$^{20}$ is cyclopropylmethyl or cyclobutylmethyl.

In yet another embodiment, "acyl" is acetyl unsubstituted or substituted with cycloalkyl, or phenyl.

In yet another embodiment, "acyl" is acetyl, lauroyl, tridecanoyl, myristoyl, pentadecanoyl, palmitoyl, caproyl, benzoyl, cetyl, decyl, acetyl, phenyl acetyl, cyclohexyl acetyl, or valeroyl.

In yet another embodiment, "acyl" is acetyl, or palmitoyl.

In yet another embodiment, "acyl" is glucuronyl residue.

In most particular embodiment, "acyl" is acetyl or MeCO—.

In one embodiment, with respect to the synthetic oligomer of formula Ia or Ib, the oligomer is selected from the oligomers listed in Table 1.

In certain aspects and where appropriate, the present invention extends to the preparation of prodrugs and derivatives of the peptoids of the invention. Prodrugs are derivatives which have cleavable groups and become by solvolysis or under physiological conditions the peptoid of the invention, which are pharmaceutically active, in vivo.

In one embodiment, the invention provides a pharmaceutical composition comprising a pharmaceutically acceptable carrier and a pharmaceutically effective amount of the peptoid of formula I.

In one embodiment, the invention provides a pharmaceutical composition of the synthetic oligomer of formula Ia or Ib, comprising a pharmaceutically acceptable carrier, and the carrier is a parenteral carrier, oral or topical carrier.

In one embodiment, the invention provides a method for preventing, treating, ameliorating or managing a disease or condition which comprises administering to a patient in need of such prevention, treatment, amelioration or management, a prophylactically or therapeutically effective amount of the pharmaceutical composition of the synthetic oligomer of formula Ia or Ib.

In one embodiment, the disease or condition is or results from neurodegeneration.

In one embodiment, the disease or condition is AD. In a particular embodiment, the disease or condition is early stage AD, prior to manifestation of mild cognitive impairment and, more particularly, when AD is only detectable on a histological level.

In one embodiment, the disease is associated with Aβ oligomerization.

In one embodiment, the invention provides a method for preventing, treating, ameliorating or managing a disease or condition, which comprises administering to a patient in need of such prevention, treatment, amelioration or management a prophylactically or therapeutically acceptable amount of a peptoid or synthetic oligomer of formula Ia or Ib, or the pharmaceutical composition thereof, wherein the disease or condition results from.

Pharmaceutical Compositions

When employed as pharmaceuticals, the peptoid compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptoid compounds in combination with one or more therapeutic compounds generally prescribed for the treatment of AD. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptoid compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, vaginal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1—Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

A compound of the invention may be admixed as a dry powder with a starch diluent in an approximate 1:1 weight ratio. The mixture is filled into 250 mg capsules (125 mg of active compound per capsule).

Formulation 3—Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) may be added and the resulting mixture is stirred until it congeals.

Methods of Treatment

The peptide/peptoid oligomers may be administered as therapeutic agents to a subject afflicted with AD. The ability of the peptide/peptoid oligomers to inhibit fibrillization and oligomerization of Aβ and to preserve glutaminergic receptors and ameliorate intraneuronal Aβ accumulation strongly suggests that oligomers of the invention will confer therapeutic benefit to subjects to whom the oligomers are administered. The pharmacokinetic profiles of the instant oligomers also indicate that these agents are resistant to enzymatic digestion (are stable), non-toxic, and possess improved blood-brain-barrier permeability.

Further to the above and in light of the results presented herein, the peptoids and compositions comprising same may be used to advantage in the prevention and/or treatment of AD. In a particular embodiment, the peptoids and compositions described herein are administered to a subject with early stage AD, prior to the onset of profound cognitive dysfunction. In a more particular embodiment, peptoids and compositions described herein are administered to a subject wherein early signs of AD are detected histologically or on the basis of imaging techniques that visualize pathology on a cellular and/or histological level (e.g., formation of Aβ fibrils and/or Aβ plaques) in the brain, which are characteristic of AD. Imaging techniques that can be used for detection directed to this purpose include, but are not limited to, positron emission tomography (PET), MRI (magnetic resonance imaging) and SPECT (single photon emission computerized tomography). Peptoids and compositions described herein may also be administered to a subject with early stage AD, wherein mild cognitive dysfunction is evident. Ideally, the peptoids and compositions described herein are administered to a subject at early stages of AD, so as to maximize the therapeutic and preventative benefits of the peptoids and compositions administered to the subject.

The complexes of this invention can be administered as the sole active agent or they can be administered in combination with other agents, including other active derivatives.

In accordance with results determined in rats, the peptoids described herein (e.g., compound of formula IXa, GKLVFNmgA, Oligomer 14; SEQ ID NO: 3) demonstrate good blood brain barrier (BBB) penetration and can be detected in the cerebrospinal fluid (CSF) following intravenous administration. High level in plasma of GKLVFNmgA (SEQ ID NO: 3) can be also observed after its intranasal delivery. Lesser level of GKLVFNmgA (SEQ ID NO: 3) in plasma is observed following its oral delivery, indicating that the peptoids are susceptible, at least in part, to the digestive enzymes in the gut. Modifications of the peptoids are thus envisioned herein, whereby the peptoids are rendered more resistant to digestive enzymes via time release formulations and modifications thereof.

The in vivo studies also revealed that the half-life of the compound of formula IXa (GKLVFNmgA, Oligomer 14; SEQ ID NO: 3) in rats is less than 2 hours, thus providing guidance pertaining to dosing parameters (e.g., to dose more frequently) and suggesting that modifications of the peptoids so as to increase half-life thereof would be advantageous. Such modifications are known to those skilled in the art.

A skilled practitioner would appreciate that the choice as to which compound or compounds of the invention are well suited to a particular application must take into consideration such variables as the severity of the disease or condition, mode of administration, and duration of administration, and the cost:benefit ratio associated with synthesis of linear versus cyclic peptoids.

Diagnostic Methods

The peptide/peptoid oligomers may be used as diagnostic agents to determine if a subject has early stage AD. The ability of the peptide/peptoid oligomers to cross the blood brain barrier and bind to Aβ monomers, fibrils, and plaques strongly suggests that peptoids of the invention can be used to detect Aβ fibrils and plaques in the brains of subjects and to, moreover, quantitate the levels of Aβ fibrils and plaques therein. Accordingly, it is envisioned that the peptoids described herein can be labeled to facilitate detection using PET or the like, particularly imaging techniques that are non-invasive, and administered to subjects for the purpose of determining levels of Aβ fibrils and plaques in the subject's brain. An exemplary label to use for such purposes is gadolinium. Accordingly, encompassed herein are peptides as described which are conjugated to a gadolinium chelate or other contrast agent known in the art for MRI and isotopes for PET/SPECT.

With regard to diagnostic applications, the peptides described herein (e.g., compound of formula IXa, GKLVFNmgA, Oligomer 14; SEQ ID NO: 3) demonstrate good blood brain barrier (BBB) penetration and can be detected in the cerebrospinal fluid (CSF) following intravenous administration.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptoid oligomers that have been listed hereinabove. The peptoid or synthetic oligomers of the invention may be prepared from known or commercially available starting materials and reagents by one skilled in the art of organic synthesis.

Solvents and reagents purchased from commercial sources were used without further purification. Abbreviations for reagents are as follows: 9-fluorenylmethoxycarbonyl (Fmoc); tert-butoxycarbonyl (Boc); benzotriazole-1-yl-oxy-tris-pyrrolidino-phosphonium hexafluorophosphate (PyBOP); Bromo-tris-pyrrolidino phosphoniumhexafluorophosphate (PyBrOP); trifluoroacetic acid (TFA); hexafluoroisopropyl alcohol (HFIP); methylene chloride (DCM); N,N'-dimethylformamide (DMF); N,N'-diisopropylcarbodiimide (DIC); diisopropylethylamine (DIEA); acetonitrile (ACN); N-methylmorpholine (NMM); O-Benzotriazole-N,N,N',N'-tetramethyl-uronium-hexafluoro-phosphate (HBTU).

Representative Synthetic Method

Preparation of Oligomers of the Invention

All peptide and Peptide-Peptoid hybrid oligomers described herein were synthesized on Rink Amide resin (0.64 mmol g$^{-1}$) (Novabiochem, San Diego, Calif.), using either standard Fmoc solid-phase peptide synthesis or modifications of the same to incorporate 'submonomer chemistry' (Figliozzi et al, Synthesis of N-substituted glycine peptoid libraries. In *Methods Enzymol.*, Academic Press: 1996; Vol. 267, pp 437-447; Bartlett et al., *Proc. Natl. Acad. Sci. U.S.A* 1992, 89, 9367-9371) wherever needed as depicted in scheme 1. Peptides and Peptides-Peptoids were synthesized in parallel using a fully automated robotic workstation (Charybdis™ Instruments) with software protocol written in-house. All peptides and Peptoids oligomers were synthesized at room temperature. Fmoc Amino Acids were purchased from Novabiochem. The submonomer amines were purchased from Alfa Aesar and Sigma-Aldrich. O-Benzotriazole-N,N,N',N'-tetramethyl-uronium-hexafluoro-phosphate (HBTU) were purchased from Novabiochem and N-methyl Morpholine (Nmm) were purchased from AlfaAesar. Bromoacetic acid was purchased from Sigma-Aldrich. N,N'diisopropylcarbodiimide (DIC) was purchased from Chem-Impex International. Trifluoroacetic acid(TFA) was purchased from Fisher Scientific. Triisopropylsilane (TIPS) was purchased from Sigma-Aldrich. Other reagents and solvents were obtained from commercial sources and used without additional purification.

Synthesis 1: Synthesis of Peptide and Peptide-Peptoid hybrid oligomers

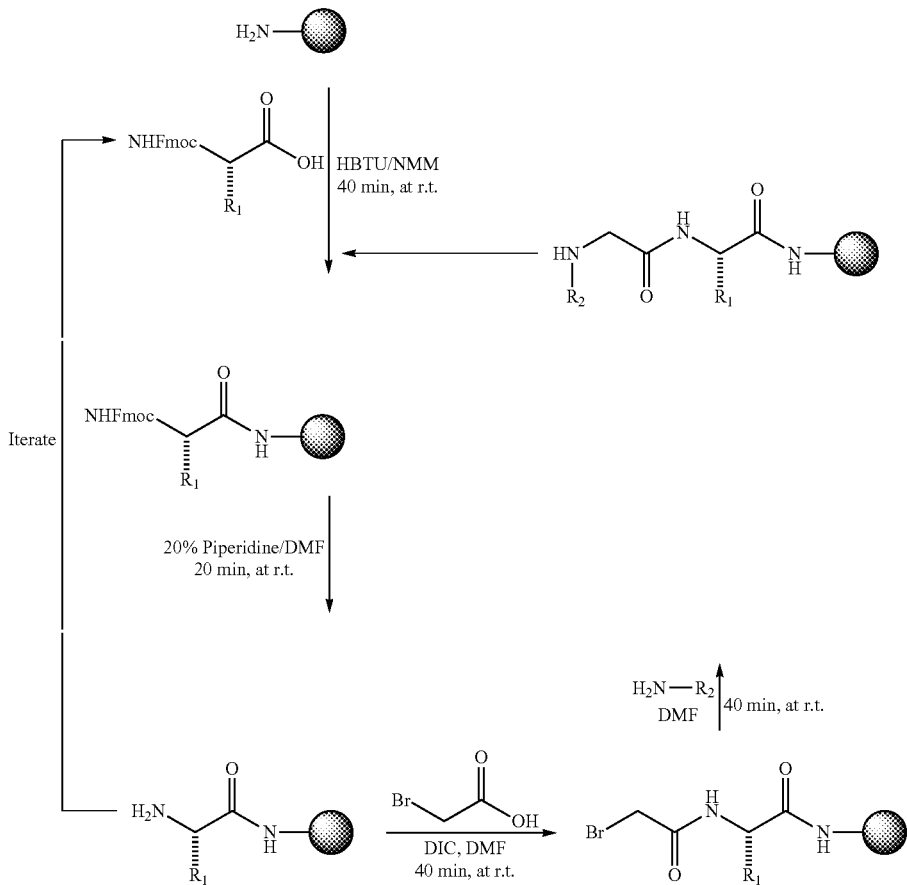

Typically, 100 mg Rink Amide resin at a loading level of 0.64 mmol g$^{-1}$ was swollen in dichloromethane (DCM) for 10 minutes (min) before starting peptide and peptide-peptoid hybrid oligomers synthesis. Multiple washing steps using dimethylforamide (DMF) were performed between each step described below. In general, the foremost step involves the removal of 9-Fluorenylmethyloxycarbonyl (Fmoc) group from rink amide resin by 1 ml 20% piperidine in DMF (2×) and was allowed to shake for 10 min each followed by multiple washes with DMF (10 mL g$^{-1}$ resin) (5×1 min). Also, the iterative two steps procedure were followed:
  i) it involves the coupling of desired amino acid, in this case, FmocAla-OH (1 ml/100 mg, 0.5 M) with the resin by using HBTU (1 ml/100 mg, 0.5 M) as coupling reagent and Nmm (1 ml/100 mg, 1.5 M) as base to load first amino acids which were needed to shake for 40 min followed by washing with DMF (10 mL, g$^{-1}$ resin) (5×1 min) to obtain the pure coupled product on resin;
  ii) the second step involve the removal of Fmoc group from the coupled amino acid by 1 ml 20% Piperidine in DMF (2×) also accompanied by washing with DMF (10 mL g$^{-1}$ resin) (5×1 min).

The above mentioned two iterative steps were typically continued until the desired sequence and length of the oligomers were obtained. All amino acid addition and Fmoc deprotection steps were performed on a robotic synthesizer (Charybdis Technologies Inc., San Diego, Calif.) until the desired peptide length was obtained. Fmoc-Sar-OH, Fmoc-Phe-OH, Fmoc-Val-OH, Fmoc-Leu-OH, and Fmoc-Lys (Boc)-OH and Fmoc-Gly-OH were purchased from Nova-Biochem (San Diego, Calif.). However, to obtain peptide-peptoid hybrid oligomer typical procedure involves the combination of solid phase peptide synthesis and modified 'submonomer' protocol (Zuckermann, R. N. et al. J. Am. Chem. Soc. 1992, 114, 10646). Once the desired sequence and length of the oligomer was obtained, the Fmoc group is removed and the appropriate peptoid residue was incorporated using the following protocol. The steps were repeated until the final peptide-peptoid hybrid was obtained. Bromoacetylation was completed by adding 20 eq bromoacetic acid (1.2 M in DMF, 8.5 mL g$^{-1}$ resin) and 24 eq of diisopropylcarbodiimide (2 mL g$^{-1}$ resin), this reaction was allowed to shake at room temperature for an 1 hour. Following the reaction, the bromoacetylation reagents were washed from the resin using DMF (10 mL g$^{-1}$ resin) (5×1 min) and 20 equivalents of submonomer amine (1.0 M in DMF, 10 mL g$^{-1}$ resin) were added (eg N-phenylmethylglycine, Npm)). The amine displacement reaction was allowed to shake at room temperature for 40 min and was followed by multiple washing steps (DMF, 10 mL g$^{-1}$ resin) (5×1 min). Bromoacetylations and amine displacement steps were repeated wherever needed in the desired sequence. After manual loading of peptoid residues in hybrid, all subsequent amino acid addition and Fmoc deprotection steps were performed on a robotic synthesizer (Charybdis Technologies Inc., San Diego, Calif.) until the desired peptide length was obtained. Almost always, The oligomers were acetylated by using Acetic Anhydride (Alfa Aesar) and DIEA (Diisopropyl Ethyl amine) (1 ml, 1.5 M) 1 ml/200 mg of resin. To cleave the peptide and peptide-peptoid hybrid oligomers from solid support for analysis, approximately 5 mg of resin was treated with 95/2.5/2.5% TFA/water/TIPS (40 mL g$^{-1}$ resin) for an hour. The cleavage cocktail was evaporated under nitrogen gas for analytical characterization. For preparative sample, ether precipitation was carried out which involves the addition of cold diethyl ether (10 ml/100 mg) in the sample to precipitate out the oligomer. The oligomers were resuspended after removing residual ether by stream of nitrogen in 1 mL HPLC solvent (1:1 HPLC grade acetonitrile:HPLC grade water). The oligomers were analyzed on a C$_{18}$ reversed-phase analytical RP-HPLC column at room temperature (Peeke Scientific, 5 μm, 120 Å, 2.0×50 mm) using a Beckman Coulter System Gold instrument. A linear gradient of 5-95% acetonitrile/water (0.1% TFA, Acros Organics) over 20 min was used with a flow rate of 0.7 mL/min for analytical characterization. In order to remove any traces of TFA in the sample solution, linear precursors dissolved in 50% ACN/H$_2$O were freeze-dried overnight for preparative HPLC.

The following oligomers are prepared following the method described herein.

The following additional oligomers are synthesized following the method described herein. Formula IXa corresponds to SEQ ID NO: 3; Formula IXb corresponds to SEQ ID NO: 3, wherein glycine at position 1 is attached to an acetyl group.

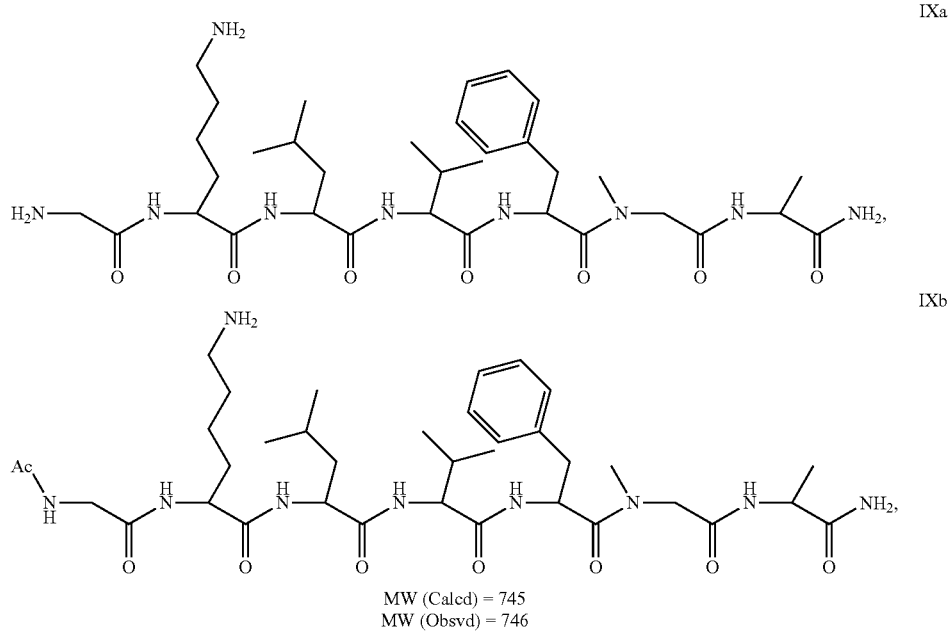

MW (Calcd) = 745
MW (Obsvd) = 746

TABLE 1

Representative Synthetic Oligomers of the Invention

| # | Oligomer |
|---|---|
| 1 | KLVFNpmA; SEQ ID NO: 5 |
| 2 | KLVNpmFA; SEQ ID NO: 6 |
| 3 | KLVNpmNpmFA; SEQ ID NO: 7 |
| 4 | KLVNchmA; SEQ ID NO: 8 |
| 5 | KLVNchmFA; SEQ ID NO: 9 |
| 6 | KLVNchmNchmA; SEQ ID NO: 10 |
| 7 | KLVFNmgA; SEQ ID NO: 11 |
| 8 | KLVNmgFA; SEQ ID NO: 12 |
| 9 | KLVFNmgNmgA; SEQ ID NO: 13 |
| 10 | KLVF(Ch-Ala)A; SEQ ID NO: 14 |
| 11 | KLV(Ch-Ala)FA; SEQ ID NO: 15 |
| 12 | KLV(Ch-Ala) (Ch-Ala)A; SEQ ID NO: 16 |
| 13 | GKLNpmFFA; SEQ ID NO: 2 |
| 14 | GKLVFNmgA; SEQ ID NO: 3 |

EXAMPLES

The following examples are presented in order to more fully illustrate the preferred embodiments of the invention. They should in no way be construed, however, as limiting the broad scope of the invention.

Example 1

Cell Culture Neurotoxicity Studies

MTT Toxicity Assay

The effect of 1-100 μmol/L concentrations of peptoid compounds on the viability of the SK-N-SH human neuroblastoma cell line (American Type Culture Collection, Manassas, Va.) was compared to the well established neurotoxicity of Aβ1-40 and Aβ1-42 in tissue culture (Sadowski et al. [2004] Am J Pathol 165, 937-948; which is hereby incorporated by reference in its entirety). SK-N-SH cells were plated at 10,000 cells/100 μl per well in flat-bottom, 96-well microtiter plates and incubated with 1-100 μmol/L concentrations of tested peptides for two days after which cell viability was assessed using a metabolic assay, which is based on cleavage of the yellow tetrazolium salt (MTT) to purple formazan crystals by viable cells. The MTT assay (Roche Molecular Biochemicals, Indianapolis, Ind.) was performed according to the manufacturer's instructions.

Handling of AD Peptides and In Vitro AD Oligomerization.

Aβ peptides were custom synthesized on solid phase support and purified by reverse phase high pressure liquid chromatogropahy, as previously described (Sadowski et al., 2004. Am. J. Pathol. 165, 937-48; Sadowski et al., 2006, Proc Natl Acad Sci USA; 103, 18787-92), the entire contents of which are incorporated herein by reference. Full length sequences of Aβ1-40 (Aβ40), Aβ1-42 (Aβ42), and Aβ1-40 N-terminally tagged with 5,6-carboxyfluorescein (FITC-Aβ40) were synthesized using L-amino acids (Sadowski et al., 2004. Am. J. Pathol. 165, 937-48; Sadowski et al., 2006, Proc Natl Acad Sci USA; 103, 18787-92). A purity of each batch of peptides was verified by mass spectrometry. Aβ peptides were treated with 1,1,1,3,3,3-hexafluoro-2-propanol (HFIP) that renders peptides monomeric with minimal β-sheet content (Sadowski et al., 2004. Am. J. Pathol. 165, 937-48; Stine et al., 2003. J. Biol. Chem. 278, 11612-22) and lyophilized. Lyophilized aliquots of Aβ peptides were stored at −80° C. Immediately prior to commencing cell culture experiments Aβ peptides were directly reconstituted in cell culture media to achieve concentration used in particular experiments.

Cell Culture Preparation.

P0-P1 pups of C57bL/6 mice were killed by decapitation and brains were removed in aseptic conditions. To establish cultures of primary hippocampal neurons the hippocampi were dissected from both hemispheres under AmScope stereoscopic microscope (AmScope, Chino, Calif.). Fragments of tissue were placed in the ice-cold $Ca^{2+}$ and $Mg^{2+}$ free Hank's balanced salt solution (HBSS) and gently cut further into fine pieces which were then treated with 0.05% trypsin in HBSS for 10 min at 37° C. to obtain cell suspension. Following addition of 0.1% type-I-S trypsin inhibitor and 0.05% DNase I, the cell suspension was centrifuged at 500×g for 30 sec. The resulting pellet was triturated, centrifuged again at 500×g for 5 min and resuspended in the minimal essential medium (MEM) supplemented with heat-inactivated 10% fetal bovine serum (FBS), 0.5 mM glutamine, streptomycin (50 µg/ml) and penicillin (50 U/ml). The cell suspension was then filtered through a 70-µm mesh, and the cells were counted using hematocytometer (Hausser Scientific, Horsham, Pa.). The cells were seeded on poly-L-lysine coated 12-well plates. For biochemical analysis $5 \times 10^5$ cells were seeded directly on the bottom of each well whereas for immunohistochemistry a removable, poly-L-lysine coated round coverslip was placed on the bottom of the well and the number of seeded cells was reduced to $1 \times 10^5$ per well. The neurons were allowed to adhere to the surface for four hours and then the medium was replaced with the serum-free Neurobasal medium containing 2% B27 supplement, 0.5 mM glutamine, streptomycin (50 µg/ml) and penicillin (50 U/ml). At three days in vitro (DIV) 5 µM of cytosine-β-D-arabinoside (Ara C) was added for 48 hr to inhibit division of non-neuronal cells. At 7 DIV one well from each preparation of primary hippocampal neurons was randomly selected to determine the purity of the culture. This was done by calculating the ratio of cells immunostained against microtubule-associated protein 2 (MAP2), which is a neuronal specific marker against all cells stained with 4',6-diamidino-2-phenylindole (DAPI) nucleic acid stain. Cultures demonstrating purity of at least 90% were grown further until 15 DIV when neurons reach mature morphology and express functional glutamatergic receptors (Mattson et al., 1991. Brain Res. 565, 94-108).

Treatments of Cell Cultures with Aβ Peptides.

Monomerized Aβ40 peptides were diluted in cell culture media and added to neuronal monocultures for 24 or 72 hr. In experiments designed to directly visualize formation of Aβ oligomers a mixture of 9 µM Aβ40 and 1 µM FITC-Aβ40 was used.

Western and Dot Immunoblotting.

Primary hippocampal neurons grown on the bottom of the well were washed three times with PBS at 37° C. and harvested with ice-cold lysis buffer containing 50 mM Tris-HCl, pH 7.4, 150 mM NaCl, 1 mM Ethylenediaminetetraacetic acid, 1% nonidet-P4, 0, 0.1% SDS, 0.2% diethylamine, 1 mM phenylmethylsulfonyl fluoride, a Complete Protease Inhibitor Cocktail 10 µg/ml supplemented with leupeptin, antipain, pepstatin (5 µg/ml each) (Sadowski et al., 2006. Proc Natl Acad Sci USA; 103, 18787-92). The lysates were collected into 2 ml low adhesion microcentrifuged, further homogenized with ten strokes of a Teflon pestle, and centrifuged at 10,000×g for 20 min at 4° C. The pellets containing cell debris were discarded while the total protein concentration in the supernatant was determined using BCA assay. Samples of cell lysates containing equal amounts of total protein were titrated with reducing Laemmli buffer to achieve equal volumes, boiled for 5 min and then subjected to SDS-PAGE, followed by Western transfer onto nitrocellulose membranes and immunoblotting as previously described (Pankiewicz et al., 2006. Eur. J. Neurosci. 23, 2635-47; Sadowski et al., 2009. Neurobiol Dis; 34, 267-78). For detection of Aβ peptides in neuronal lysates 1:1 mixture of 6E10 and 4G8 monoclonal Abs was used for increased sensitivity. HRP conjugated secondary antibodies were used in 1:3,000 dilutions.

Densitometric Analysis.

Autoradiography films were converted into 8 bit grayscale digital files using a Epson Perfection 4990 scanner (Epson America; Long Beach, Calif.) and Adobe Photoshop CS4 (Adobe Systems; San Jose, Calif.) and saved in a TIF format with a resolution of 600 dpi. Densitometric analysis of Western and dot-blot signals was performed using NIH Image J software v 1.42 (Bethesda, Md.) as previously described (Pankiewicz et al., 2006. Eur. J. Neurosci. 23, 2635-47; Sadowski et al., 2009. Neurobiol Dis; 34, 267-78).

Immunocytochemistry and Quantification of Synaptic Protein Expression.

Coverslip inserts covered by the primary hippocampal neuro"s were immersed three times in PBS at 37° C., and then in 80% ice-cold methanol for 10 min to fix the neurons, and washed again three times in PBS. Non-specific binding of the primary Abs and streptavidin was blocked using MOM blocking mixture for 1 hr followed by the Streptavidin/Biotin blocking kit for 30 min. Synaptic proteins specific for excitatory glutamatergic synapses of primary hippocampal neurons including the NR1 subunit of the N-methyl-D-aspartic acid receptors (NMDARs), post-synaptic density protein 95 (PSD-95), which is functionally and structurally associated with NMDARs, and synaptophysin were immunodetected using specific monoclonal antibodies against the C-terminus of NR1 subunit of NMDAR (1:2,000; Millipore Corp., Billerica, Mass.), PSD-95 (1:500; Millipore Corp., Billerica, Mass.), and synaptophysin (1:500; Santa Cruz Biotechnology, Santa Cruz, USA)". Biotinylated secondary antibodies (1:1,000) followed by Cy3 conjugated streptavidine (1:500) were used to detected binding of primary Abs to their antigens. Neuronal nuclei were counterstained with DAPI. Immunostained neurons were analyzed under 80i Nikon fluorescent microscope (Nikon Corp. Tokyo, Japan). To determine expression of synaptic proteins at least 20 neurons from each treatment group per experiment from three independent experiments were photographed using ×100 immersion oil objective. The images were captured using a high-sensitivity, cooled, monochrome DS-Qi1Mc camera and NIS Elements Imaging Software (Nikon Corp. Tokyo, Japan) and saved in a TIF format with a resolution of 600 dpi. Using NIH Image J software v 1.42 (Bethesda, Md.) five rectangular tests areas measuring 20×4 µM each were randomly superimposed along the primary and secondary dendrites of each examined neuron, with the long axis of the test area oriented parallel to the long axis of the dendrites. Synaptic densities within the test area were automatically thresholded and filtered according to the preset algorithm to discriminate nonspecific staining. Data were expressed as the percent values using as 100% the average from the total area of synaptic proteins puncta per test field in DIV-matched control primary hippocampal neurons.

Figure 2:
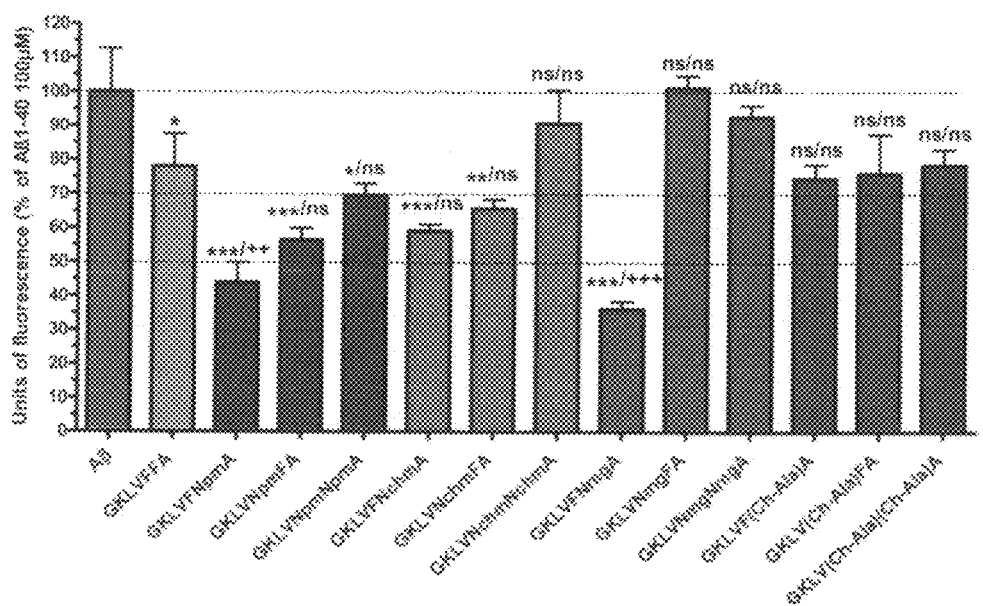
FIG. 2 shows (A) sequences of tested peptide/peptoid hybrid compounds. (B) shows a histogram bar graph depicting results from a Thioflavine-T aggregation assay. 100 µM of Aβ1-40 was aggregated in the presence of tested compounds (10:1 ratio) for 96 hr. *p<0.05; p<0.01; *p<0.001 vs control Aβ; +p<0.05; ++p<0.01; +++p<0.001 vs Aβ+GKLVFFA (SEQ ID NO: 1). One-way ANOVA followed by Dunnet post-hoc test. Sequences listed therein are as follows: GKLVFFA (SEQ ID NO: 1), GKLVFNmgA (SEQ ID NO: 3), KLVFFA (SEQ ID NO: 4), KLVFNpmA (SEQ ID NO: 5), KLVNpmFA (SEQ ID NO: 6), KLVNpmNpmFA (SEQ ID NO: 7), KLVFNchmA (SEQ ID NO: 8), KLVNchmFA (SEQ ID NO: 9), KLVNchmNchmA (SEQ ID NO: 10), KLVFNmgA (SEQ ID NO: 11), KLVNmgFA (SEQ ID NO: 12), KLVNmgNmgA (SEQ ID NO: 13), KLVF(Ch-Ala)A (SEQ ID NO: 14), KLV(Ch-Ala)FA (SEQ ID NO: 15), KLV(Ch-Ala)(Ch-Ala)A (SEQ ID NO: 16), GKLVNpmFA (SEQ ID NO: 17), GKLVNpmNpmA (SEQ ID NO: 18), GKLVFNchmA (SEQ ID NO: 19), GKLVNchmFA (SEQ ID NO: 20), GKLVNchmNchmA (SEQ ID NO: 21), GKLVFNpmA (SEQ ID NO: 22), GKLVNmgFA (SEQ ID NO: 23), GKLVNmgNmgA (SEQ ID NO: 24), GKLVF(Ch-Ala)A (SEQ ID NO: 25), GKLV(Ch-Ala)FA (SEQ ID NO: 26), and GKLV(Ch-Ala)(Ch-Ala)A (SEQ ID NO: 27).

The sequence Aβ17-21 of AB is well known to form into a β-sheet conformation, which is correlated with its ability to aggregate and to cause cellular toxicity. Accordingly, the present inventors modified the sequence Aβ16-21(KLVFFA; SEQ ID NO: 4), so as to generate compounds that do not possess the aggregation and toxicity properties of the full length AB sequence. To this end, a library of peptide/peptoid hybrids of Aβ16-21(KLVFFA; SEQ ID NO: 4) sequence was synthesized using various N-substituted glycine peptoids to replace amino acids at different positions and characterized. The rationale was that the absence of amide group hydrogen in peptoids prevents formation of hydrogen bonds facilitating β-sheet folding, and in effect prevents toxicity associated with formation of β-sheet pleated aggregates. FIG. 1 demonstrates that a single position peptoid modification of the KLVFFA (SEQ ID NO: 4) sequence prevents its toxicity in SK-N-SH human neuroblastoma cells using MTT toxicity assay. FIG. 2 shows the effect of compounds incorporating various peptoid monomers into the KLVFFA (SEQ ID NO: 4) sequence on the aggregation of Aβ40. The results depicted in FIG. 2 clearly demonstrate that some of newly developed peptide/peptoid hybrids have strong anti-fibrillization properties. An exemplary compound, GKLVFNmgA (SEQ ID NO: 3), was selected for further characterization with regard to its pharmacodynamic effects using in vitro and cell culture models.

GKLVFNmgA (SEQ ID NO: 3) Prevents Aβ Fibrillization and Oligomerization Thioflavine-T Aggregation Assay Peptoid modified derivatives of the KLVFFA (SEQ ID NO: 4) sequence were tested using Thioflavine-T aggregation assay to determine whether or not they are capable of forming fibrils themselves. Synthetic Aβ1-40 and Aβ1-42 with well established fibrillogenic potentials were used for comparison. Having established that peptoid modified derivatives of KLVFFA (SEQ ID NO: 4) sequence do not aggregate themselves into fibrils, they were subsequently tested to determine if they can prevent fibrillization of Aβ1-40 and Aβ1-42. In these treatment experiments, 100 μM Aβ40 or Aβ42 was mixed with 1-100 μM of of the investigated compound and incubated up to 14 days. AB aggregation and Thioflavine-T assays were conducted according to our previously published protocols (Sadowski eta 1. [2004] Am J Pathol 165, 937-948; which is hereby incorporated by reference in its entirety). Aβ1-40 and Aβ1-42 were HFIP (hexafluoroisopropanol) treated and reconstituted in 100 mM Tris buffer to obtain 100 μmol/L concentration. They were incubated alone or in the presence of peptoid modified derivatives of KLVFFA (SEQ ID NO: 4) sequence at concentrations of 1-100 μM. In addition, peptoid modified derivatives of KLVFFA (SEQ ID NO: 4) sequence were incubated alone as indicated above at the concentration of 100 μM. At the indicated intervals, samples containing 15 μg of incubated peptides were added to 1 mL of 50 mM/L glycine, pH 9.2 and 2 μM/L of Thioflavin-T (Sigma Chemical, Co.; St. Louis, Mo.). Fluorescence was measured at excitation 435 nm and emission 485 nm in a Hitachi F-2000 fluorescence spectrophotometer. A time scan of fluorescence was performed and three values after the decay reached a plateau (280, 290, 300 seconds) were averaged. The background fluorescence of 40 μl of Tris buffer added to 2 μM/L of Thioflavin-T solution was subtracted. Samples were run in duplicate. Differences in amount of fibrils formed by different peptides at particular time points were evaluated by one-way ANOVA followed by Tukey post hoc test. GKLVFNmgA (SEQ ID NO: 3) did not form fibrils itself even at a concentration 100 μM and showed a strong dose dependent effect on aggregation of Aβ1-40. See FIG. 3.

Oligomerization Assay

The present inventors have also investigated whether GKLVFNmgA (SEQ ID NO: 3) prevents assembly of Aβ1-40 into oligomers irrespective of its anti-fibrillization properties. The rationale is that Aβ oligomeric assemblies are particularly toxic to synaptic components and impair neurotransmission. HFIP treated Aβ1-40 was oligomerized in DMEM/F12 medium with 0.2% SDS at 4° C. for 24 h, alone or with addition of [10 μM] GKLVFNmgA (SEQ ID NO: 310:1 Aβ:inhibitor ratio). Prior to electrophoresis, glutaraldehyde (0.4 mM final concentration) was added to prevent disassembly of complexes. Samples were immediately subjected to electrophoresis in non-reducing condition, Western-transfer, and detection with a mixture of 4G8 and 6E10 anti-Aβ Mabs. Densitometric analysis of the membranes using Image J 1.40 g revealed reduction of oligomers in treated GKLVFNmgA SEQ ID NO: 3) sample by 61.3% (p<0.05; Mann-Whitney U-Test). See FIG. 4.

GKLVFNmgA (SEQ ID NO: 3) Prevents Synaptic Degeneration

Oligomers of Aβ formed in the extracellular space are known to bind to the surface of neurons, preferentially at glutaminergic receptors, thereby affecting their expression and function. FIG. 5 Panel I shows a neuron from a primary hippocampal neuronal culture in 18 day in vivo (DIV) immunostained with a monoclonal antibody against NR1 subunit of NMDA glutaminergic receptor, which was exposed to oligomeric aggregates of FITC labeled Aβ40 (A). As seen in the magnified portion of the picture, Aβ oligomers preferentially colocalize in the areas with greater NR1 expression (arrows) (A'). Reduction in the number of AB aggregates can be seen in neurons treated with GKLVFNmgA (SEQ ID NO: 3) (B). Binding of Aβ aggregates to surface expressed NMDA receptors leads to their downregulation. FIG. 5, Panel II shows partial loss of staining against subunit NR1 of the NMDA receptor, (B) post-synaptic density protein 95 (PSD-95), which is structurally and physiologically associated with NMDA receptor, and (C) synaptophysin in 18 DIV cultures of primary hippocampal neurons exposed to 10 μM of Aβ40 for 72 hr. This loss was partially prevented when GKLVFNmgA (SEQ ID NO: 3) [5 μM] was added to the medium together with Aβ40. Results of quantification of NR1 subunits positive densities are shown in FIG. 5 Panel III. While exposure of 18 DIV primary hippocampal neurons to 10 μM Aβ40 oligomers resulted in down regulation of NR1 NMDA receptor subunit to 48.6% of the control, along with synaptophysin and PSD-95 positive densities to 45.3% and 50.2% of the control, respectively (p<0.001). Co-treatment with 5 μM GKLVFNmgA (SEQ ID NO: 3) significantly ameliorated loss of NR1, synaptophysin, and PSD-95 expression by altering their levels to 83%, 84.5% and 82.3% of the control values, respectively; (p<0.001). Treatment of neurons with GKLVFNmgA (SEQ ID NO: 3) alone had no significant effect on the expression of these three synaptic proteins. The results presented herein indicate that peptide/peptoid compounds containing N-methyl-glycine show therapeutic activities in vivo preventing loss of excitatory synapses containing glutaminergic receptors.

GKLVFNmgA Ameliorates Intraneuronal Aβ Accumulation

Figure 6A:
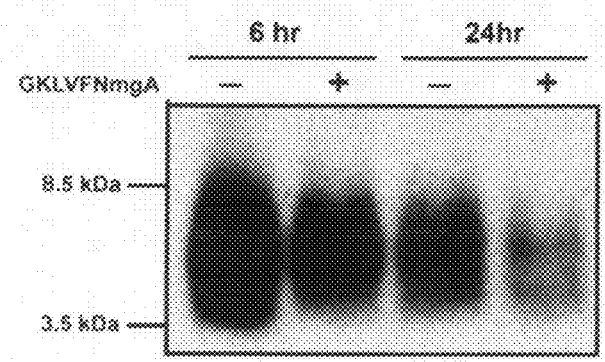
FIG. 6. (A) Shown is a reduction in the amount of internally accumulated AB in 15 DIV primary hippocampal neurons exposed to 10 µM of Aβ in the absence and presence of 5 of GKLVFNmgA (SEQ ID NO: 3) for 6 and 24 hr. Lysates of primary hippocampal neurons were subjected to SDS-PAGE electrophoresis in reducing conditions and following the Western transfer, the membranes were immunostained with a mixture of 6E10 and 4G8 monoclonal antibodies (1:10,000). (B) Shown is densitometric analysis of the Western-blots depicted in (A). Neurons treated with GKLVFNmgA (SEQ ID NO: 3) accumulated 29.8% and 49.3% less AB after six and 24 hr of exposure, respectively ($p<0.01$, unpaired two-tailed t-test).
Figure 6B:
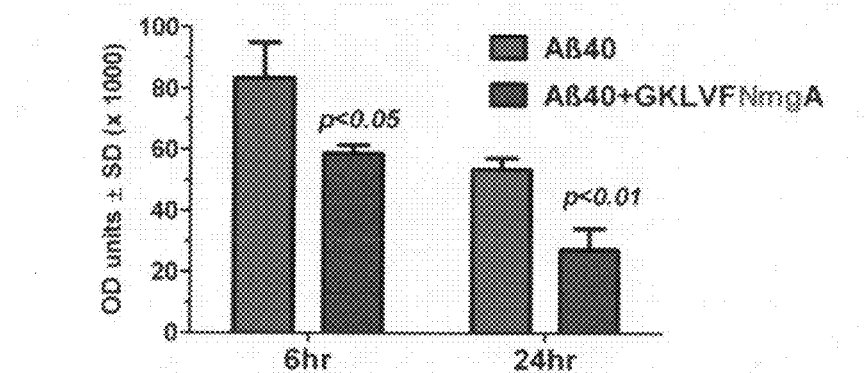

Treatment with GKLVFNmgA (SEQ ID NO: 3) also appears to reduce intraneuronal Aβ accumulation. FIG. 6 shows the amount of Aβ in lysates from 16 DIV primary hippocampal neurons exposed to 10 μM of Aβ40 for 6 or 24 hr in the absence or presence of GKLVFNmgA (SEQ ID NO: 3). FIG. 6B shows densitometric analysis of Western-blots, which correspond to samples shown in FIG. 5A. Neurons treated with GKLVFNmgA (SEQ ID NO: 3) accumulated 29.8% and 49.3% fewer AB molecules after six and 24 hr of exposure, respectively (p<0.01). The results presented herein indicate that peptide/peptoid compounds containing N-methyl-glycine show therapeutic activities in vivo ameliorating intraneuronal AB accumulation.

Example 2

GKLVFNmgA (SEQ ID NO: 3) Affects Aβ Metabolism in AD Transgenic Mice Methods for Microdialysis In Vivo Microdialysis.

Mice were anesthetized with an intraperitoneal injection of Ketamine (50 mg/kg) and Xylazine (10 mg/kg). An MBR-10 guide cannula was stereotactically implanted into the right hippocampus (bregma −3.1 mm, 2.4 mm lateral, 12° angle). Four hours later mice were anesthetized again for the insertion of a BR-4 microdialysis probe with 38 kDa molecular weight cutoff (MWCO) membrane (Cirrito et al., 2008. 2008. Neuron; 58, 42-51) which was introduced through the implanted guide cannula. The probe was positioned so that the microdialysis membrane was almost entirely embedded in the strata radiatum and lacunosum-moleculare of the CA1 hippocampal sector (FIG. 8A). The probe was connected to a syringe pump (Stoelting Co., Wood Dale, Ill.) and a refrigerated sample collector (Univentor Ltd., Malta) using teflon (FEP) tubing (SciPro Inc., Sanborn, N.Y.) and perfused at the constant rate of 1 μL/min with artificial cerebrospinal fluid (aCSF) (1.3 mM $CaCl_2$, 1.2 mM $MgSO_4$, 3 mM KCl, 0.4 mM $KH_2PO_4$, 25 mM $NaHCO_3$, and 122 mM NaCl, pH 7.35) containing 0.15% bovine serum albumin (BSA) (Cirrito et al., 2003. J. Neurosci. 23, 8844-53; the entire contents of which is incorporated herein in its entirety). After recovering from anesthesia mice were placed in the Raturn Cage Systems designed to allow unrestricted animal movements without applying pressure to probe assembly. The animals were perfused with aCSF for 16 hr allowing for healing and closure of the blood-brain-barrier and for animals to adapt to new environment.

Aβ Quantification.

eAβ level in the ISF dialyzate was determined using sandwich ELISA specific for human $Aβ_{1-x}$. Monoclonal antibodies 6E10 (Aβ residues 1-16) and biotynylated 4G8 (Aβ residues 17-24) (Sadowski et al., 2006. Proc Natl Acad Sci USA; 103, 18787-92) were used as capture and detection antibodies, respectively. The antibody 4G8 was biotynylated using EZ-Link Sulfo-NHS-Biotin Biotinylation Kit (Pierce, Rockford, Ill.), following the manufacturer's manual. Polystyrene microtiter plates (Immulon-2, Dynatech Lab.; Chantilly, Va.) were coated overnight at 4° C. with 6E10 monoclonal antibody in the amount of 2 μg/well. Non-specific binding was blocked with 4% BSA diluted in 0.01 phosphate buffered saline, for 60 min at 37° C. Undiluted dialysate samples and samples of formic acid treated synthetic Aβ40 serially diluted from 1200 pg/mL to 1.65 pg/mL were applied overnight at 4° C., followed by biotynylated monoclonal antibody 4G8 (1 μg/mL), which was added for 90 min and incubated at 37° C. Then the streptavidin-poly-horseradish peroxidase-40 (Research Diagnostics, Flanders, N.J.) was added followed by Slow ELISA TMB and 2M sulfuric acid to stop the reaction. Absorbance was read on the Epoch Microplate Spectrophotometer (BioTek Instruments, Inc. Winooski, Vt.). Following background subtraction, absorbance values from serially diluted synthetic Aβ samples were used to generate a standard curve in GraphPad Prism v5.02 (GraphPad Software, Inc., San Diego) using a non-linear curve-fitting algorithm. eAβ concentration in dialysate samples was determined by comparing their absorbance values against the standard curve.

As depicted in FIG. 8, the in vivo effect of GKLVFNmgA (SEQ ID NO: 3) was investigated using Aβ microdialysis in awake and behaving AD Tg mice. Aβ microdialysis measures the pool of soluble Aβ in the brain interstitial fluid (ISF), dubbed eAβ, which is permeable through a membrane with 34 kDa molecular weight cutoff eAβ includes mainly AB monomers, with some contribution of dimers and trimers, but does not include larger AB oligomers or AB coupled to carrier proteins. Delivery of 100 μM GKLVFNmgA (SEQ ID NO: 3) through reverse microdialysis into the CA1 area of the hippocampus (FIG. 8A) of nine months old $APP_{SW}/PS1_{L166P}$ AD transgenic mice resulted in substantial increases in the concentration of $eAβ_{1-x}$ in the dialysate. The increase in eAβ concentration was observed from the seventh hour after the infusion onset and attained a maximal effect between hours 9 and 16 of the infusion, ranging between 250 and 300% of the basal ISF value. (FIG. 8B). The results presented herein indicate that peptide/peptoid compounds containing N-methyl-glycine show therapeutic activities in vivo increasing soluble AB level in the ISF in AD Tg mice. Anti-aggregation compounds containing N-methyl-glycine can thus improve AB clearance and prevent downstream neurodegenerative cascades initiated by accumulation of AB in the brain.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for peptoid oligomers are approximate, and are provided for description.

It is also understood that the synthetic oligomers or compounds of the invention are capped with the appropriate X and Y groups. If not shown then it is understood that the end groups are appropriately H or $NH_2$.

All publications, including but not limited to patents and patent applications, cited in this specification are herein incorporated by reference as if each individual publication were specifically and individually indicated to be incorporated by reference herein as though fully set forth.

What is claimed is:

1. A synthetic oligomer
   (i) wherein the synthetic oligomer is
   X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y (SEQ ID NO: 28);
   or a salt thereof, and stereoisomers, isotopic variants and tautomers thereof;
   and wherein at least one and up to 35 amino acid residues are replaced with monomers independently selected from Nap, Nab, Nah, Ngb, Npm, Nnm, Ndp, Nip, Nib, Nmg, and Nchm;
   or
   (ii) wherein the synthetic oligomer is X-Gly-Lys-Leu-Val-Phe-Phe-Ala-Glu-Asp-Val-Gly-Y (SEQ ID NO: 32); or a salt thereof, and stereoisomers, isotopic variants and tautomers thereof; and wherein at least one and up to 5 amino acid residues are replaced with monomers independently selected from Nap, Nab, Nah, Ngb, Npm, Nnm, Ndp, Nip, Nib, Nmg, and Nchm;
   or
   (iii) wherein the synthetic oligomer is X-Gly-Lys-Leu-Val-Phe-Phe-Ala-Glu-Y (SEQ ID NO: 33); or a salt thereof, and stereoisomers, isotopic variants and tautomers thereof;
   and wherein at least one and up to 4 amino acid residues are replaced with monomers independently selected from Nap, Nab, Nah, Ngb, Npm, Nnm, Ndp, Nip, Nib, Nmg, and Nchm;
   or
   (iv) wherein the synthetic oligomer is X-Gly-Lys-Leu-Val-Phe-Phe-Y (SEQ ID NO: 34); or a salt thereof, and stereoisomers, isotopic variants and tautomers thereof; and wherein at least one and up to 4 amino acid residues are replaced with monomers independently selected from Nap, Nab, Nah, Ngb, Npm, Nnm, Ndp, Nip, Nib, Nmg, and Nchm;
   and wherein:

Phe is phenylalanine or cyclohexylalanine;

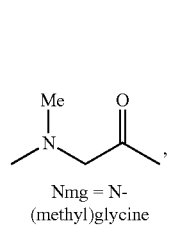

Nmg = N-(methyl)glycine

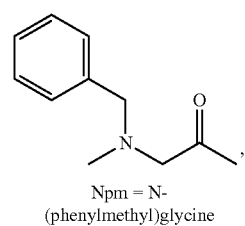

Npm = N-(phenylmethyl)glycine

-continued

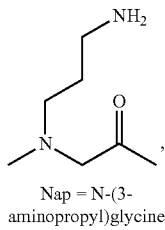
Nap = N-(3-aminopropyl)glycine

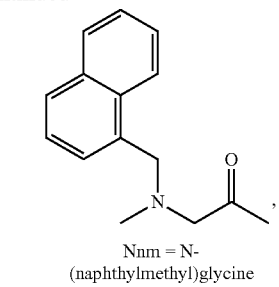
Nnm = N-(naphthylmethyl)glycine

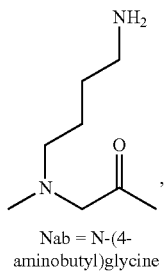
Nab = N-(4-aminobutyl)glycine

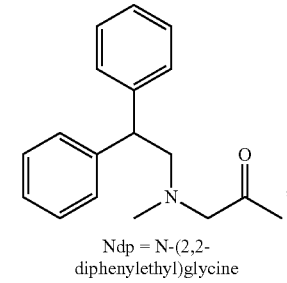
Ndp = N-(2,2-diphenylethyl)glycine

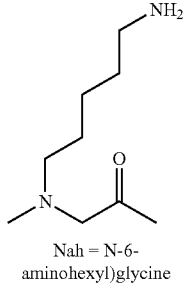
Nah = N-6-aminohexyl)glycine

Nip = N-(isopropyl)glycine

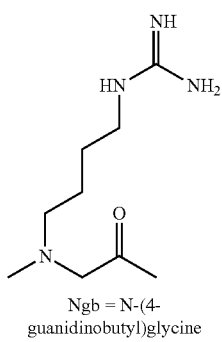
Ngb = N-(4-guanidinobutyl)glycine

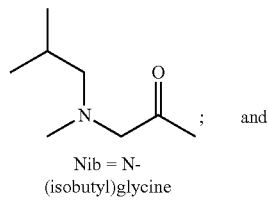
Nib = N-(isobutyl)glycine ; and

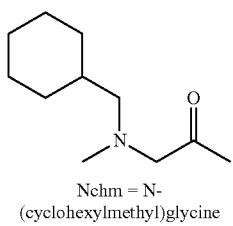
Nchm = N-(cyclohexylmethyl)glycine and provided that a) the monomer or monomers adjacent to Nmg are other than Gly, Nmg, Ser, Ile, or Tyr; and b) none of -Gly-residues is replaced with Nmg.

2. The synthetic oligomer according to claim 1, wherein the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y; and
at least one and up to 5 amino acid residues of -His-His-Gln-Lys-Leu-Val-Phe-Phe-Ala- (SEQ ID NO: 29) are replaced with monomers independently selected from Nap, Nab, Nah, Ngb, Npm, Nnm, Ndp, Nip, Nib, Nmg, and Nchm.

3. The synthetic oligomer according to claim 1, wherein the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y; and
at least one and up to 4 amino acid residues of -Gln-Lys-Leu-Val-Phe-Phe-Ala- (SEQ ID NO: 30) are replaced with monomers independently selected from Nap, Nab, Nah, Ngb, Npm, Nnm, Ndp, Nip, Nib, Nmg, and Nchm.

4. The synthetic oligomer according to claim 1, wherein the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y; and
at least one and up to 3 amino acid residues of -Lys-Leu-Val-Phe-Phe-Ala- (SEQ ID NO: 4) are replaced with monomers independently selected from Nap, Nab, Nah, Ngb, Npm, Nnm, Ndp, Nip, Nib, Nmg, and Nchm.

5. The synthetic oligomer according to claim 1, wherein the synthetic oligomer is
X-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-Y; and
at least one and up to 2 amino acid residues of -Leu-Val-Phe-Phe-Ala- (SEQ ID NO: 31) are replaced with monomers independently selected from Nap, Nab, Nah, Ngb, Npm, Nnm, Ndp, Nip, Nib, Nmg, and Nchm.

6. The synthetic oligomer according to claim 1, wherein the synthetic oligomer is X-Gly-Lys-Leu-Val-Phe-Phe-Ala-Glu-Asp-Val-Gly-Y (SEQ ID NO: 32); and wherein at least one and up to 5 amino acid residues are replaced independently with monomers according to formula IIa, IIb, or IIc or with amino acid residues independently selected from Nap, Nab, Nah, Ngb, Npm, Nnm, Ndp, Nip, Nib, Nmg, and Nchm.

7. The synthetic oligomer according to claim 1, wherein the synthetic oligomer is X-Gly-Lys-Leu-Val-Phe-Phe-Ala-Glu-Y (SEQ ID NO: 33); and wherein at least one and up to 4 amino acid residues are replaced independently with monomers according to formula IIa, IIb, or IIc or with amino acid residues independently selected from Nap, Nab, Nah, Ngb, Npm, Nnm, Ndp, Nip, Nib, Nmg, and Nchm.

8. The synthetic oligomer according to claim 1, wherein the synthetic oligomer is X-Gly-Lys-Leu-Val-Phe-Phe-Y (SEQ ID NO: 34); and wherein at least one and up to 4 amino acid residues are replaced independently with monomers according to formula IIa, IIb, or IIc or with amino acid residues independently selected from Nap, Nab, Nah, Ngb, Npm, Nnm, Ndp, Nip, Nib, Nmg, and Nchm.

9. A synthetic oligomer according to formula IIIa (SEQ ID NO: 36), IIIb (SEQ ID NO: 36), IIIc (SEQ ID NO: 37), IIId (SEQ ID NO: 37), IIIe (SEQ ID NO: 38) or IIIf (SEQ ID NO: 38):

X—⁅GKLVFFA⁆ₜ—Y,  (IIIa)

⁅GKLVFFA⁆ₜ  (IIIb)

X—⁅KLVFFA⁆ₜ—Y,  (IIIc)

⁅KLVFFA⁆ₜ  (IIId)

X—⁅QLVFFA⁆ₜ—Y or  (IIIe)

⁅QLVFFA⁆ₜ,  (IIIf)

or a salt thereof; and stereoisomers, isotopic variants and tautomers thereof;

wherein F is phenylalanine or cyclohexylalanine;

t is an integer from 1-5;

X is H, or substituted or unsubstituted acyl; Y is $NH_2$, OH, acylamino, or acyloxy;

at least one and up to 3 of K, Q, L, V, F, and A of IIIa, IIIb, IIIc, IIId, IIIe, or IIIf are independently replaced with monomers according to formula IIa, IIb, or IIc:

(IIa) structure with $R^{1a}$ (IIb) structure with $R^{1b}$ or (IIc) structure with $R^{1c}$;

each $R^{1a}$ is independently unsubstituted alkyl or cycloalkylalkyl;

each $R^{1b}$ is independently aminoalkyl, guanidinoalkyl ($H_2N$—C(=NH)—NH-alkyl) or methyl, n-propyl, n-butyl, n-pentyl, or n-hexyl; and each of methyl, n-propyl, n-butyl, n-pentyl, and n-hexyl is independently substituted with pyrrolyl, imidazolyl, oxazolyl, isoxazolyl, thiazolyl, thiadiazolyl, or tetrazolyl;

each $R^{1c}$ is independently substituted or unsubstituted aryl, substituted or unsubstituted aralkyl, or substituted or unsubstituted diarylalkyl; or $R^{1c}$ is furanyl or thienyl, each of which unsubstituted or substituted with one or more groups selected from alkyl, halo, hydroxy, amino, nitro, and alkoxy;

provided that when the amino acid residue K is replaced with the monomer according to formula IIa, then $R^{1a}$ is other than Me.

10. A synthetic oligomer is according to formula IIIa (SEQ ID NO: 36), IIIb (SEQ ID NO: 36), IIIc (SEQ ID NO: 37), IIId (SEQ ID NO: 37), IIIe (SEQ ID NO: 38) or IIIf (SEQ ID NO: 38):

X—⁅GKLVFFA⁆ₜ—Y,  (IIIa)

⁅GKLVFFA⁆ₜ  (IIIb)

X—⁅KLVFFA⁆ₜ—Y,  (IIIc)

⁅KLVFFA⁆ₜ  (IIId)

X—⁅QLVFFA⁆ₜ—Y or  (IIIe)

⁅QLVFFA⁆ₜ,  (IIIf)

or a salt thereof; and stereoisomers, isotopic variants and tautomers thereof;

wherein F is phenylalanine or cyclohexylalanine;

t is an integer from 1-5;

X is H, or substituted or unsubstituted acyl; Y is $NH_2$, OH, acylamino, or acyloxy;

at least one and up to 3 of K, Q, L, V, F, and A of each of IIIa, IIIb, IIIc, IIId, IIIe, or IIIf are independently replaced with monomers independently selected from Nap, Nab, Nah, Ngb, Npm, Nnm, Ndp, Nip, Nib, Nmg, and Nchm; and wherein:

Nmg = N-(methyl)glycine

Npm = N-(phenylmethyl)glycine

Nap = N-(3-aminopropyl)glycine

Nnm = N-(naphthylmethyl)glycine

Nab = N-(4-aminobutyl)glycine

Ndp = N-(2,2-diphenylethyl)glycine

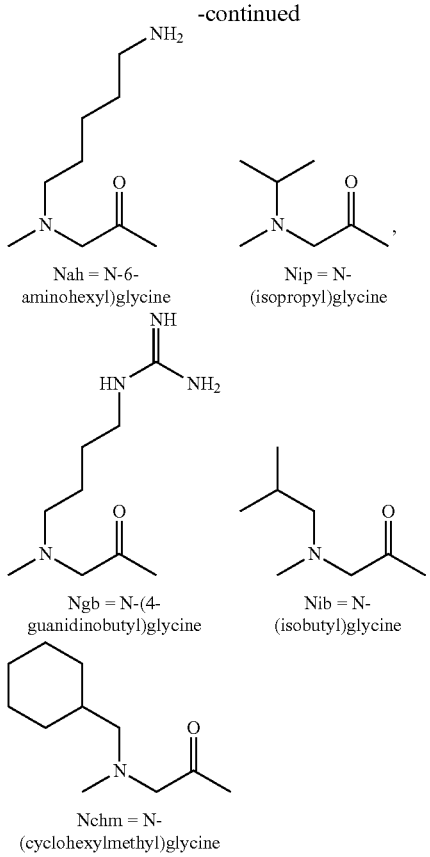

X is H, or substituted or unsubstituted acyl; and Y is NH₂, OH, acylamino, or acyloxy;

provided that the synthetic oligomer is other than

(SEQ ID NO: 39)

11. The synthetic oligomer according to claim 10, wherein at least one of K, L, V, F, and A of -(KLVFFA)- (SEQ ID NO: 37) is independently replaced with N-phenylmethylglycine (Npm), N-cyclohexylmethylamine (Nchm), or N-methylglycine (Nmg); or
at least one of Q, L, V, F, and A of -(QLVFFA)- (SEQ ID NO: 38) is independently replaced with N-phenylmethylglycine (Npm), N-cyclohexylmethylamine (Nchm), or N-methylglycine (Nmg).

12. The synthetic oligomer according to claim 10, wherein one or both Fs of -(KLVFFA)- (SEQ ID NO: 37) or -(QLVFFA)- (SEQ ID NO: 38) are independently replaced with N-phenylmethylglycine (Npm), N-cyclohexylmethylamine (Nchm), or N-methylglycine (Nmg).

13. The synthetic oligomer according to claim 10, wherein the synthetic oligomer is X-(GKLVFNpmA)$_t$-Y (SEQ ID NO: 40), X-(GKLVNpmFA)$_t$-Y (SEQ ID NO: 41), X-(GKLVFNchmA)$_t$-Y (SEQ ID NO: 42), X-(GKLVNchmFA)$_t$-Y (SEQ ID NO: 43), X-(GKLVNmgFA)$_t$-Y (SEQ ID NO: 45), X-(GKLVNpmNpmA)$_t$-Y (SEQ ID NO: 46), X-(GKLVNchmNchmA)$_t$-Y (SEQ ID NO: 47), or X-(GKLVFNmgA)$_t$-Y (SEQ ID NO: 44); the subscript t is 1 or 2; X is acetyl or H; and Y is NH₂.

14. The synthetic oligomer according to claim 10, wherein the synthetic oligomer is according to formula IVa (SEQ ID NO: 22), IVb (SEQ ID NO: 17), IVc (SEQ ID NO: 18), Va (SEQ ID NO: 3), Vb (SEQ ID NO: 23), VIa (SEQ ID NO: 19), VIb (SEQ ID NO: 20), VIc (SEQ ID NO: 21), or VII (SEQ ID NO: 50; SEQ ID NO: 2; or SEQ ID NO: 49):

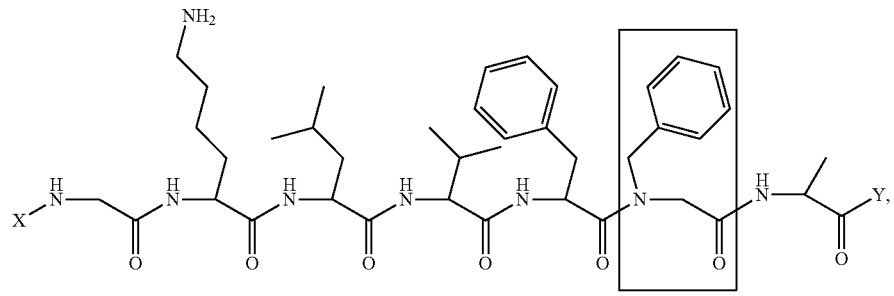

IVa

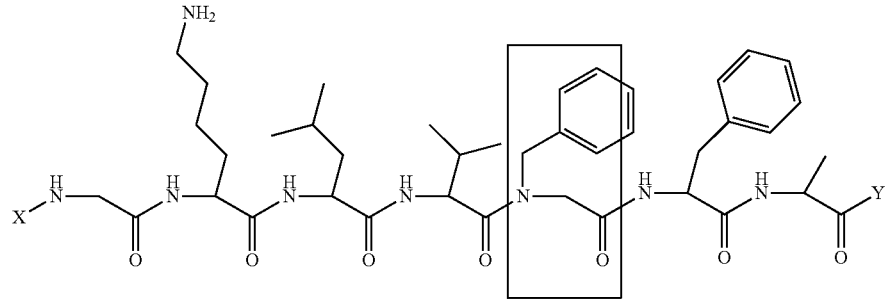

IVb

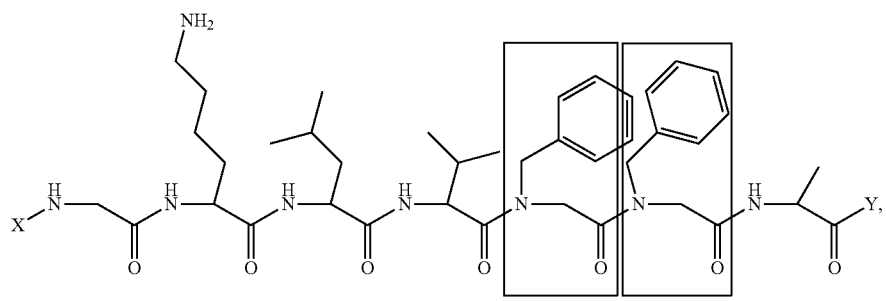
IVc
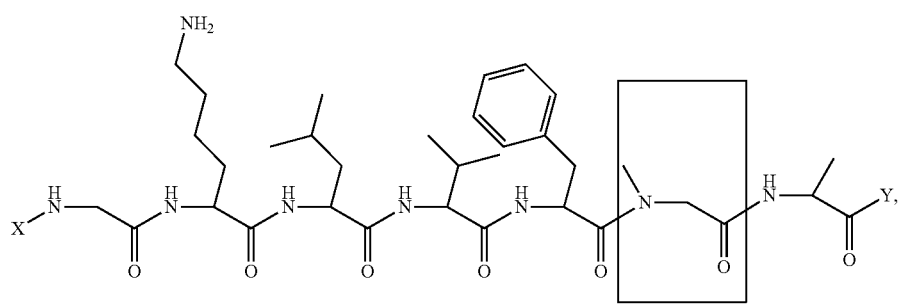
Va
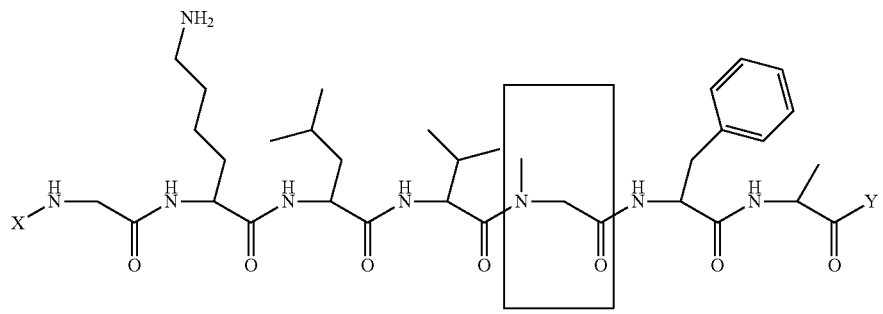
Vb
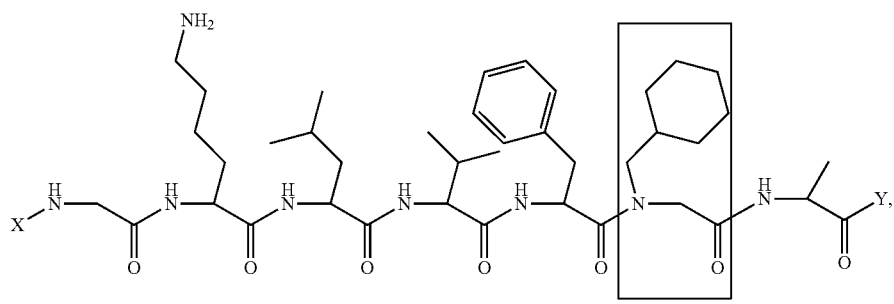
VIa
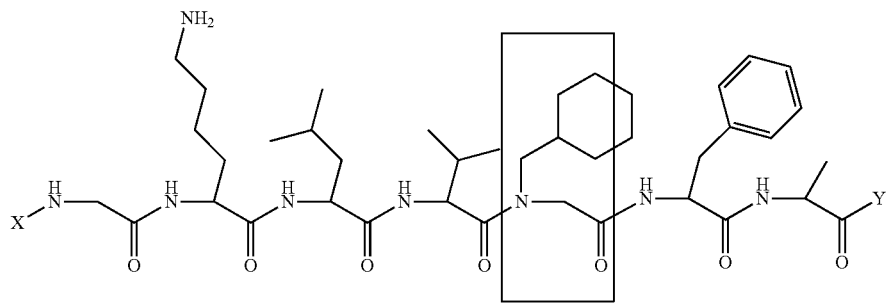
VIb

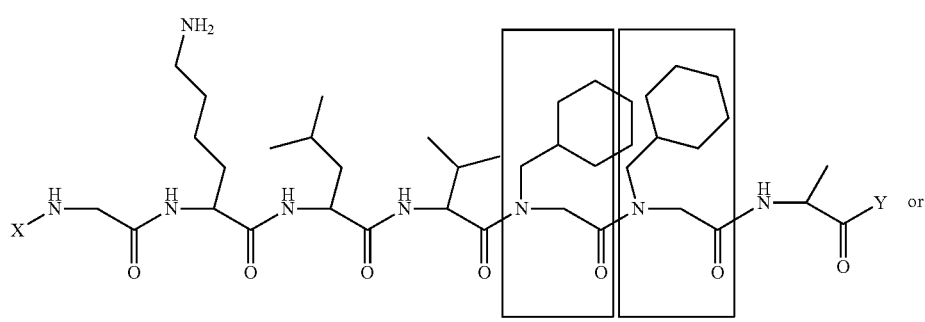

VIc

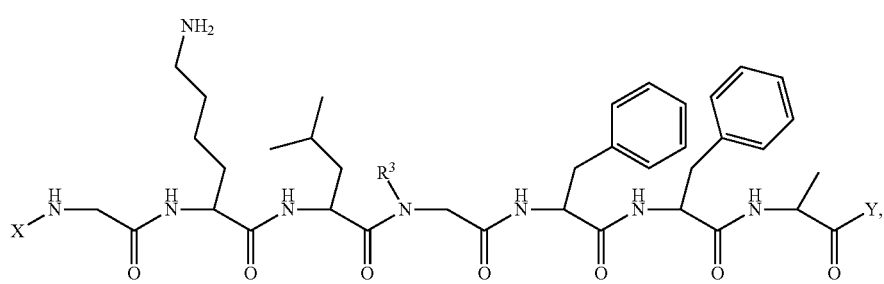

VII or a salt thereof, and stereoisomers, isotopic variants and tautomers thereof;
wherein X is acetyl or H; Y is $NH_2$; and $R^3$ is Me, phenylmethyl, or cyclohexylmethyl.

15. The synthetic oligomer according to any one of claims 1, 9, or 10, wherein X is H or unsubstituted acyl.

16. The synthetic oligomer according to any one of claims 1, 9, or 10, wherein Y is $NH_2$.

17. The synthetic oligomer according to claim 10, wherein the synthetic oligomer is according to formula IXa (SEQ ID NO: 3) or IXb (SEQ ID NO: 3):

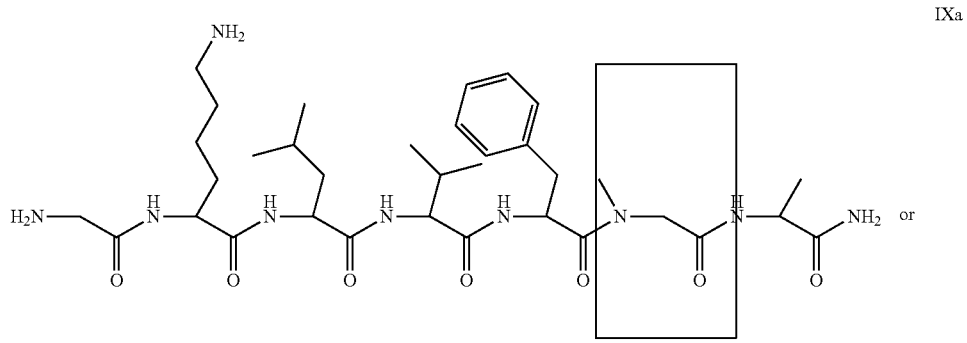

IXa or

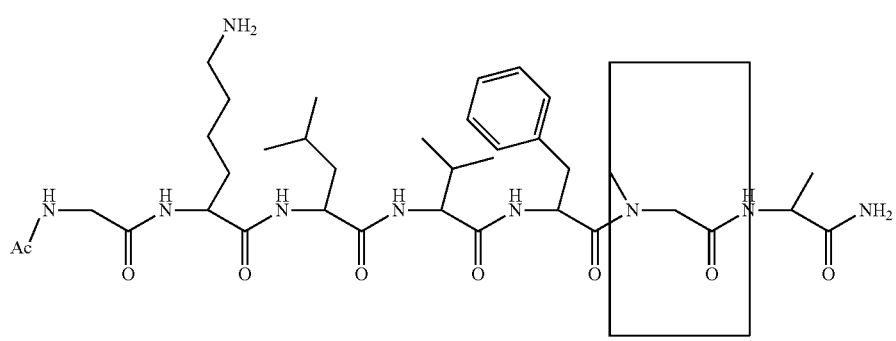

IXb or a salt thereof, and stereoisomers, isotopic variants and tautomers thereof.

18. A pharmaceutical composition comprising a pharmaceutically acceptable carrier and a pharmaceutically effective amount of the synthetic oligomer of any one of claims 1, 9, or 10.

19. The pharmaceutical composition of claim 18 wherein the carrier is a parenteral, oral or topical carrier.

20. A method for treating, ameliorating or managing a disease or condition which comprises administering to a patient in need of such treatment, amelioration or management, a therapeutically effective amount of the pharmaceutical composition of the synthetic oligomer of any one of claims 1, 9, or 10.

21. The method of claim 20, wherein the disease or condition is or results from neurodegeneration.

\* \* \* \* \*

SEQUENCE LISTING

<160> NUMBER OF SEQ ID NOS: 50

<210> SEQ ID NO 1
<211> LENGTH: 7
<212> TYPE: PRT
<213> ORGANISM: Homo sapiens

```
<400> SEQUENCE: 1

Gly Lys Leu Val Phe Phe Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-phenylmethylglycine

<400> SEQUENCE: 2

Gly Lys Leu Xaa Phe Phe Ala
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (1)..(1)
<223> OTHER INFORMATION: Glycine can be attached to an acetyl group or
      not
<220> FEATURE:
<221> NAME/KEY: misc_feature
<222> LOCATION: (6)..(6)
<223> OTHER INFORMATION: Xaa is N-Methylglycine

<400> SEQUENCE: 3

Gly Lys Leu Val Phe Xaa Ala
1               5

<210> SEQ ID NO 4
<211> LENGTH: 6
<212> TYPE: PRT
<213> ORGANISM: Homo sapiens

<400> SEQUENCE: 4

Lys Leu Val Phe Phe Ala
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-phenylmethylglycine

<400> SEQUENCE: 5

Lys Leu Val Phe Xaa Ala
1               5

<210> SEQ ID NO 6
<211> LENGTH: 6
<212> TYPE: PRT
<213> ORGANISM: Artificial Sequence
<220> FEATURE:
```

<223> OTHER INFORMATION: Synthetic peptoid
<220> FEATURE:
<221> NAME/KEY: misc_feature
<222> LOCATION: (4)..(4)
<223> OTHER INFORMATION: Xaa is N-phenylmethylglycine

<400> SEQUENCE: 6

Lys Leu Val Xaa Phe Ala
 1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-phenylmethylglycinel
<220> FEATURE:
<221> NAME/KEY: misc_feature
<222> LOCATION: (5)..(5)
<223> OTHER INFORMATION: Xaa is N-phenylmethylglycine

<400> SEQUENCE: 7

Lys Leu Val Xaa Xaa Phe Ala
 1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-cyclohexylmethylglycine

<400> SEQUENCE: 8

Lys Leu Val Phe Xaa Ala
 1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-cyclohexylmethylglycine

<400> SEQUENCE: 9

Lys Leu Val Xaa Phe Ala
 1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-cyclohexylmethylglycine
<220> FEATURE:
<221> NAME/KEY: misc_feature

```
<222> LOCATION: (5)..(5)
<223> OTHER INFORMATION: Xaa is N-cyclohexylmethylglycine

<400> SEQUENCE: 10

Lys Leu Val Xaa Xaa Ala
 1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-Methylglycine

<400> SEQUENCE: 11

Lys Leu Val Phe Xaa Ala
 1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-Methylglycine

<400> SEQUENCE: 12

Lys Leu Val Xaa Phe Ala
 1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-Methylglycine
<220> FEATURE:
<221> NAME/KEY: misc_feature
<222> LOCATION: (6)..(6)
<223> OTHER INFORMATION: Xaa is N-Methylglycine

<400> SEQUENCE: 13

Lys Leu Val Phe Xaa Xaa Ala
 1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is Cyclohexylalanine

<400> SEQUENCE: 14

Lys Leu Val Phe Xaa Ala
 1               5
```

```
<210> SEQ ID NO 15
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is Cyclohexylalanine

<400> SEQUENCE: 15

Lys Leu Val Xaa Phe Ala
 1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is Cyclohexylalanine
<220> FEATURE:
<221> NAME/KEY: misc_feature
<222> LOCATION: (5)..(5)
<223> OTHER INFORMATION: Xaa is Cyclohexylalanine

<400> SEQUENCE: 16

Lys Leu Val Xaa Xaa Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-phenylmethylglycine

<400> SEQUENCE: 17

Gly Lys Leu Val Xaa Phe Ala
 1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-phenylmethylglycine
<220> FEATURE:
<221> NAME/KEY: misc_feature
<222> LOCATION: (6)..(6)
<223> OTHER INFORMATION: Xaa is N-phenylmethylglycine

<400> SEQUENCE: 18

Gly Lys Leu Val Xaa Xaa Ala
 1               5

<210> SEQ ID NO 19
```

```
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is N-cyclohexylmethylglycine

<400> SEQUENCE: 19

Gly Lys Leu Val Phe Xaa Ala
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-cyclohexylmethylglycine

<400> SEQUENCE: 20

Gly Lys Leu Val Xaa Phe Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-cyclohexylmethylglycine
<220> FEATURE:
<221> NAME/KEY: misc_feature
<222> LOCATION: (6)..(6)
<223> OTHER INFORMATION: Xaa is N-cyclohexylmethylglycine

<400> SEQUENCE: 21

Gly Lys Leu Val Xaa Xaa Ala
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is N-phenylmethylglycine

<400> SEQUENCE: 22

Gly Lys Leu Val Phe Xaa Ala
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
```

```
<222> LOCATION: (5)..(5)
<223> OTHER INFORMATION: Xaa is N-Methylglycine

<400> SEQUENCE: 23

Gly Lys Leu Val Xaa Phe Ala
 1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-Methylglycine
<220> FEATURE:
<221> NAME/KEY: misc_feature
<222> LOCATION: (6)..(6)
<223> OTHER INFORMATION: Xaa is N-Methylglycine

<400> SEQUENCE: 24

Gly Lys Leu Val Xaa Xaa Ala
 1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is Cyclohexylalanine

<400> SEQUENCE: 25

Gly Lys Leu Val Phe Xaa Ala
 1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is Cyclohexylalanine

<400> SEQUENCE: 26

Gly Lys Leu Val Xaa Phe Ala
 1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is Cyclohexylalanine
<220> FEATURE:
<221> NAME/KEY: misc_feature
<222> LOCATION: (6)..(6)
<223> OTHER INFORMATION: Xaa is Cyclohexylalanine
```

```
<400> SEQUENCE: 27

Gly Lys Leu Val Xaa Xaa Ala
 1               5

<210> SEQ ID NO 28
<211> LENGTH: 42
<212> TYPE: PRT
<213> ORGANISM: Homo sapiens

<400> SEQUENCE: 28

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 29
<211> LENGTH: 9
<212> TYPE: PRT
<213> ORGANISM: Homo sapiens

<400> SEQUENCE: 29

His His Gln Lys Leu Val Phe Phe Ala
 1               5

<210> SEQ ID NO 30
<211> LENGTH: 7
<212> TYPE: PRT
<213> ORGANISM: Homo sapiens

<400> SEQUENCE: 30

Gln Lys Leu Val Phe Phe Ala
 1               5

<210> SEQ ID NO 31
<211> LENGTH: 5
<212> TYPE: PRT
<213> ORGANISM: Homo sapiens

<400> SEQUENCE: 31

Leu Val Phe Phe Ala
 1               5

<210> SEQ ID NO 32
<211> LENGTH: 11
<212> TYPE: PRT
<213> ORGANISM: Homo sapiens

<400> SEQUENCE: 32

Gly Lys Leu Val Phe Phe Ala Glu Asp Val Gly
 1               5                  10

<210> SEQ ID NO 33
<211> LENGTH: 8
<212> TYPE: PRT
<213> ORGANISM: Homo sapiens

<400> SEQUENCE: 33

Gly Lys Leu Val Phe Phe Ala Glu
 1               5

<210> SEQ ID NO 34
```

-continued

```
<211> LENGTH: 6
<212> TYPE: PRT
<213> ORGANISM: Homo sapiens

<400> SEQUENCE: 34

Gly Lys Leu Val Phe Phe
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic peptoid
<220> FEATURE:
<221> NAME/KEY: misc_feature
<222> LOCATION: (2)..(2)
<223> OTHER INFORMATION: Xaa is N-Methylglycine

<400> SEQUENCE: 35

Gly Xaa Leu Val Phe Phe Ala
1               5

<210> SEQ ID NO 36
<211> LENGTH: 35
<212> TYPE: PRT
<213> ORGANISM: Homo sapiens
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent
<220> FEATURE:
<221> NAME/KEY: misc_feature
<222> LOCATION: (1)..(35)
<223> OTHER INFORMATION: Head-to-tail cyclization can be present or
      absent

<400> SEQUENCE: 36

Gly Lys Leu Val Phe Phe Ala Gly Lys Leu Val Phe Phe Ala Gly Lys
1               5                   10                  15

Leu Val Phe Phe Ala Gly Lys Leu Val Phe Phe Ala Gly Lys Leu Val
            20                  25                  30

Phe Phe Ala
        35

<210> SEQ ID NO 37
<211> LENGTH: 30
<212> TYPE: PRT
<213> ORGANISM: Homo sapiens
<220> FEATURE:
<221> NAME/KEY: misc_feature
<222> LOCATION: (7)..(12)
<223> OTHER INFORMATION: All of amino acids 7-12 can be present or
      absent
<220> FEATURE:
```

```
<221> NAME/KEY: misc_feature
<222> LOCATION: (13)..(18)
<223> OTHER INFORMATION: All of amino acids 13-18 can be present or
      absent
<220> FEATURE:
<221> NAME/KEY: misc_feature
<222> LOCATION: (19)..(24)
<223> OTHER INFORMATION: All of amino acids 19-24 can be present or
      absent
<220> FEATURE:
<221> NAME/KEY: misc_feature
<222> LOCATION: (25)..(30)
<223> OTHER INFORMATION: All of amino acids 25-30 can be present or
      absent
<220> FEATURE:
<221> NAME/KEY: misc_feature
<222> LOCATION: (1)..(30)
<223> OTHER INFORMATION: Head-to-tail cyclization can be present or
      absent

<400> SEQUENCE: 37

Lys Leu Val Phe Phe Ala Lys Leu Val Phe Phe Ala Lys Leu Val Phe
 1               5                  10                  15

Phe Ala Lys Leu Val Phe Phe Ala Lys Leu Val Phe Phe Ala
             20                  25                  30

<210> SEQ ID NO 38
<211> LENGTH: 30
<212> TYPE: PRT
<213> ORGANISM: Homo sapiens
<220> FEATURE:
<221> NAME/KEY: misc_feature
<222> LOCATION: (7)..(12)
<223> OTHER INFORMATION: All of amino acids 7-12 can be present or
      absent
<220> FEATURE:
<221> NAME/KEY: misc_feature
<222> LOCATION: (13)..(18)
<223> OTHER INFORMATION: All of amino acids 13-18 can be present or
      absent
<220> FEATURE:
<221> NAME/KEY: misc_feature
<222> LOCATION: (19)..(24)
<223> OTHER INFORMATION: All of amino acids 19-24 can be present or
      absent
<220> FEATURE:
<221> NAME/KEY: misc_feature
<222> LOCATION: (25)..(30)
<223> OTHER INFORMATION: All of amino acids 25-30 can be present or
      absent
<220> FEATURE:
<221> NAME/KEY: misc_feature
<222> LOCATION: (1)..(30)
<223> OTHER INFORMATION: Head-to-tail cyclization can be present or
      absent

<400> SEQUENCE: 38

Gln Leu Val Phe Phe Ala Gln Leu Val Phe Phe Ala Gln Leu Val Phe
 1               5                  10                  15

Phe Ala Gln Leu Val Phe Phe Ala Gln Leu Val Phe Phe Ala
             20                  25                  30

<210> SEQ ID NO 39
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (2)..(2)
<223> OTHER INFORMATION: Xaa is N-Methylglycine
<220> FEATURE:
```

```
<221> NAME/KEY: misc_feature
<222> LOCATION: (9)..(9)
<223> OTHER INFORMATION: Xaa is N-Methylglycine
<220> FEATURE:
<221> NAME/KEY: misc_feature
<222> LOCATION: (16)..(16)
<223> OTHER INFORMATION: Xaa is N-Methylglycine
<220> FEATURE:
<221> NAME/KEY: misc_feature
<222> LOCATION: (23)..(23)
<223> OTHER INFORMATION: Xaa is N-Methylglycine
<220> FEATURE:
<221> NAME/KEY: misc_feature
<222> LOCATION: (30)..(30)
<223> OTHER INFORMATION: Xaa is N-Methylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 39

Gly Xaa Leu Val Phe Phe Ala Gly Xaa Leu Val Phe Phe Ala Gly Xaa
 1               5                  10                  15

Leu Val Phe Phe Ala Gly Xaa Leu Val Phe Phe Ala Gly Xaa Leu Val
            20                  25                  30

Phe Phe Ala
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is N-phenylmethylglycine
<220> FEATURE:
<221> NAME/KEY: misc_feature
<222> LOCATION: (13)..(13)
<223> OTHER INFORMATION: Xaa is N-phenylmethylglycine
<220> FEATURE:
<221> NAME/KEY: misc_feature
<222> LOCATION: (20)..(20)
<223> OTHER INFORMATION: Xaa is N-phenylmethylglycine
<220> FEATURE:
<221> NAME/KEY: misc_feature
<222> LOCATION: (27)..(27)
<223> OTHER INFORMATION: Xaa is N-phenylmethylglycine
<220> FEATURE:
<221> NAME/KEY: misc_feature
<222> LOCATION: (34)..(34)
<223> OTHER INFORMATION: Xaa is N-phenylmethylglycine
<220> FEATURE:
<221> NAME/KEY: misc_feature
<222> LOCATION: (8)..(14)
<223> OTHER INFORMATION: All of amino acids 8-14 can be present or
      absent
```

```
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 40

Gly Lys Leu Val Phe Xaa Ala Gly Lys Leu Val Phe Xaa Ala Gly Lys
1               5                   10                  15

Leu Val Phe Xaa Ala Gly Lys Leu Val Phe Xaa Ala Gly Lys Leu Val
            20                  25                  30

Phe Xaa Ala
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-phenylmethylglycine
<220> FEATURE:
<221> NAME/KEY: misc_feature
<222> LOCATION: (12)..(12)
<223> OTHER INFORMATION: Xaa is N-phenylmethylglycine
<220> FEATURE:
<221> NAME/KEY: misc_feature
<222> LOCATION: (19)..(19)
<223> OTHER INFORMATION: Xaa is N-phenylmethylglycine
<220> FEATURE:
<221> NAME/KEY: misc_feature
<222> LOCATION: (26)..(26)
<223> OTHER INFORMATION: Xaa is N-phenylmethylglycine
<220> FEATURE:
<221> NAME/KEY: misc_feature
<222> LOCATION: (33)..(33)
<223> OTHER INFORMATION: Xaa is N-phenylmethylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 41

Gly Lys Leu Val Xaa Phe Ala Gly Lys Leu Val Xaa Phe Ala Gly Lys
1               5                   10                  15
```

```
Leu Val Xaa Phe Ala Gly Lys Leu Val Xaa Phe Ala Gly Lys Leu Val
            20                  25                  30

Xaa Phe Ala
        35

<210> SEQ ID NO 42
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is N-cyclohexylmethylglycine
<220> FEATURE:
<221> NAME/KEY: misc_feature
<222> LOCATION: (13)..(13)
<223> OTHER INFORMATION: Xaa is N-cyclohexylmethylglycine
<220> FEATURE:
<221> NAME/KEY: misc_feature
<222> LOCATION: (20)..(20)
<223> OTHER INFORMATION: Xaa is N-cyclohexylmethylglycine
<220> FEATURE:
<221> NAME/KEY: misc_feature
<222> LOCATION: (27)..(27)
<223> OTHER INFORMATION: Xaa is N-cyclohexylmethylglycine
<220> FEATURE:
<221> NAME/KEY: misc_feature
<222> LOCATION: (34)..(34)
<223> OTHER INFORMATION: Xaa is N-cyclohexylmethylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 42

Gly Lys Leu Val Phe Xaa Ala Gly Lys Leu Val Phe Xaa Ala Gly Lys
1               5                   10                  15

Leu Val Phe Xaa Ala Gly Lys Leu Val Phe Xaa Ala Gly Lys Leu Val
            20                  25                  30

Phe Xaa Ala
        35

<210> SEQ ID NO 43
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-cyclohexylmethylglycine
<220> FEATURE:
<221> NAME/KEY: misc_feature
```

```
<222> LOCATION: (12)..(12)
<223> OTHER INFORMATION: Xaa is N-cyclohexylmethylglycine
<220> FEATURE:
<221> NAME/KEY: misc_feature
<222> LOCATION: (19)..(19)
<223> OTHER INFORMATION: Xaa is N-cyclohexylmethylglycine
<220> FEATURE:
<221> NAME/KEY: misc_feature
<222> LOCATION: (26)..(26)
<223> OTHER INFORMATION: Xaa is N-cyclohexylmethylglycine
<220> FEATURE:
<221> NAME/KEY: misc_feature
<222> LOCATION: (33)..(33)
<223> OTHER INFORMATION: Xaa is N-cyclohexylmethylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 43

Gly Lys Leu Val Xaa Phe Ala Gly Lys Leu Val Xaa Phe Ala Gly Lys
 1               5                  10                  15

Leu Val Xaa Phe Ala Gly Lys Leu Val Xaa Phe Ala Gly Lys Leu Val
            20                  25                  30

Xaa Phe Ala
        35

<210> SEQ ID NO 44
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (6)..(6)
<223> OTHER INFORMATION: Xaa is N-Methylglycine
<220> FEATURE:
<221> NAME/KEY: misc_feature
<222> LOCATION: (13)..(13)
<223> OTHER INFORMATION: Xaa is N-Methylglycine
<220> FEATURE:
<221> NAME/KEY: misc_feature
<222> LOCATION: (20)..(20)
<223> OTHER INFORMATION: Xaa is N-Methylglycine
<220> FEATURE:
<221> NAME/KEY: misc_feature
<222> LOCATION: (27)..(27)
<223> OTHER INFORMATION: Xaa is N-Methylglycine
<220> FEATURE:
<221> NAME/KEY: misc_feature
<222> LOCATION: (34)..(34)
<223> OTHER INFORMATION: Xaa is N-Methylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
```

```
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 44

Gly Lys Leu Val Phe Xaa Ala Gly Lys Leu Val Phe Xaa Ala Gly Lys
 1               5                  10                  15

Leu Val Phe Xaa Ala Gly Lys Leu Val Phe Xaa Ala Gly Lys Leu Val
            20                  25                  30

Phe Xaa Ala
        35

<210> SEQ ID NO 45
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-Methylglycine
<220> FEATURE:
<221> NAME/KEY: misc_feature
<222> LOCATION: (12)..(12)
<223> OTHER INFORMATION: Xaa is N-Methylglycine
<220> FEATURE:
<221> NAME/KEY: misc_feature
<222> LOCATION: (19)..(19)
<223> OTHER INFORMATION: Xaa is N-Methylglycine
<220> FEATURE:
<221> NAME/KEY: misc_feature
<222> LOCATION: (26)..(26)
<223> OTHER INFORMATION: Xaa is N-Methylglycine
<220> FEATURE:
<221> NAME/KEY: misc_feature
<222> LOCATION: (33)..(33)
<223> OTHER INFORMATION: Xaa is N-Methylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 45

Gly Lys Leu Val Xaa Phe Ala Gly Lys Leu Val Xaa Phe Ala Gly Lys
 1               5                  10                  15
```

Leu Val Xaa Phe Ala Gly Lys Leu Val Xaa Phe Ala Gly Lys Leu Val
            20                  25                  30

Xaa Phe Ala
      35

<210> SEQ ID NO 46
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-phenylmethylglycine
<220> FEATURE:
<221> NAME/KEY: misc_feature
<222> LOCATION: (6)..(6)
<223> OTHER INFORMATION: Xaa is N-phenylmethylglycine
<220> FEATURE:
<221> NAME/KEY: misc_feature
<222> LOCATION: (12)..(12)
<223> OTHER INFORMATION: Xaa is N-phenylmethylglycine
<220> FEATURE:
<221> NAME/KEY: misc_feature
<222> LOCATION: (13)..(13)
<223> OTHER INFORMATION: Xaa is N-phenylmethylglycine
<220> FEATURE:
<221> NAME/KEY: misc_feature
<222> LOCATION: (19)..(19)
<223> OTHER INFORMATION: Xaa is N-phenylmethylglycine
<220> FEATURE:
<221> NAME/KEY: misc_feature
<222> LOCATION: (20)..(20)
<223> OTHER INFORMATION: Xaa is N-phenylmethylglycine
<220> FEATURE:
<221> NAME/KEY: misc_feature
<222> LOCATION: (26)..(26)
<223> OTHER INFORMATION: Xaa is N-phenylmethylglycine
<220> FEATURE:
<221> NAME/KEY: misc_feature
<222> LOCATION: (27)..(27)
<223> OTHER INFORMATION: Xaa is N-phenylmethylglycine
<220> FEATURE:
<221> NAME/KEY: misc_feature
<222> LOCATION: (33)..(33)
<223> OTHER INFORMATION: Xaa is N-phenylmethylglycine
<220> FEATURE:
<221> NAME/KEY: misc_feature
<222> LOCATION: (34)..(34)
<223> OTHER INFORMATION: Xaa is N-phenylmethylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 46

Gly Lys Leu Val Xaa Xaa Ala Gly Lys Leu Val Xaa Xaa Ala Gly Lys
1               5                   10                  15

-continued

```
Leu Val Xaa Xaa Ala Gly Lys Leu Val Xaa Xaa Ala Gly Lys Leu Val
         20                  25                  30

Xaa Xaa Ala
        35
```

<210> SEQ ID NO 47
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-cyclohexylmethylglycine
<220> FEATURE:
<221> NAME/KEY: misc_feature
<222> LOCATION: (6)..(6)
<223> OTHER INFORMATION: Xaa is N-cyclohexylmethylglycine
<220> FEATURE:
<221> NAME/KEY: misc_feature
<222> LOCATION: (12)..(12)
<223> OTHER INFORMATION: Xaa is N-cyclohexylmethylglycine
<220> FEATURE:
<221> NAME/KEY: misc_feature
<222> LOCATION: (13)..(13)
<223> OTHER INFORMATION: Xaa is N-cyclohexylmethylglycine
<220> FEATURE:
<221> NAME/KEY: misc_feature
<222> LOCATION: (19)..(19)
<223> OTHER INFORMATION: Xaa is N-cyclohexylmethylglycine
<220> FEATURE:
<221> NAME/KEY: misc_feature
<222> LOCATION: (20)..(20)
<223> OTHER INFORMATION: Xaa is N-cyclohexylmethylglycine
<220> FEATURE:
<221> NAME/KEY: misc_feature
<222> LOCATION: (26)..(26)
<223> OTHER INFORMATION: Xaa is N-cyclohexylmethylglycine
<220> FEATURE:
<221> NAME/KEY: misc_feature
<222> LOCATION: (27)..(27)
<223> OTHER INFORMATION: Xaa is N-cyclohexylmethylglycine
<220> FEATURE:
<221> NAME/KEY: misc_feature
<222> LOCATION: (33)..(33)
<223> OTHER INFORMATION: Xaa is N-cyclohexylmethylglycine
<220> FEATURE:
<221> NAME/KEY: misc_feature
<222> LOCATION: (34)..(34)
<223> OTHER INFORMATION: Xaa is N-cyclohexylmethylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 47

```
Gly Lys Leu Val Xaa Xaa Ala Gly Lys Leu Val Xaa Xaa Ala Gly Lys
1               5                   10                  15
```

```
Leu Val Xaa Xaa Ala Gly Lys Leu Val Xaa Xaa Ala Gly Lys Leu Val
        20                  25                  30

Xaa Xaa Ala
    35

<210> SEQ ID NO 48
<211> LENGTH: 35
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (5)..(5)
<223> OTHER INFORMATION: Xaa is N-Methylglycine
<220> FEATURE:
<221> NAME/KEY: misc_feature
<222> LOCATION: (6)..(6)
<223> OTHER INFORMATION: Xaa is N-Methylglycine
<220> FEATURE:
<221> NAME/KEY: misc_feature
<222> LOCATION: (12)..(12)
<223> OTHER INFORMATION: Xaa is N-Methylglycine
<220> FEATURE:
<221> NAME/KEY: misc_feature
<222> LOCATION: (13)..(13)
<223> OTHER INFORMATION: Xaa is N-Methylglycine
<220> FEATURE:
<221> NAME/KEY: misc_feature
<222> LOCATION: (19)..(19)
<223> OTHER INFORMATION: Xaa is N-Methylglycine
<220> FEATURE:
<221> NAME/KEY: misc_feature
<222> LOCATION: (20)..(20)
<223> OTHER INFORMATION: Xaa is N-Methylglycine
<220> FEATURE:
<221> NAME/KEY: misc_feature
<222> LOCATION: (26)..(26)
<223> OTHER INFORMATION: Xaa is N-Methylglycine
<220> FEATURE:
<221> NAME/KEY: misc_feature
<222> LOCATION: (27)..(27)
<223> OTHER INFORMATION: Xaa is N-Methylglycine
<220> FEATURE:
<221> NAME/KEY: misc_feature
<222> LOCATION: (33)..(33)
<223> OTHER INFORMATION: Xaa is N-Methylglycine
<220> FEATURE:
<221> NAME/KEY: misc_feature
<222> LOCATION: (34)..(34)
<223> OTHER INFORMATION: Xaa is N-Methylglycine
<220> FEATURE:
<221> NAME/KEY: misc_feature
<222> LOCATION: (8)..(14)
<223> OTHER INFORMATION: All of amino acids 8-14 can be present or
      absent
<220> FEATURE:
<221> NAME/KEY: misc_feature
<222> LOCATION: (15)..(21)
<223> OTHER INFORMATION: All of amino acids 15-21 can be present or
      absent
<220> FEATURE:
<221> NAME/KEY: misc_feature
<222> LOCATION: (22)..(28)
<223> OTHER INFORMATION: All of amino acids 22-28 can be present or
      absent
<220> FEATURE:
<221> NAME/KEY: misc_feature
<222> LOCATION: (29)..(35)
<223> OTHER INFORMATION: All of amino acids 29-35 can be present or
      absent

<400> SEQUENCE: 48

Gly Lys Leu Val Xaa Xaa Ala Gly Lys Leu Val Xaa Xaa Ala Gly Lys
 1               5                  10                  15
```

```
Leu Val Xaa Xaa Ala Gly Lys Leu Val Xaa Xaa Ala Gly Lys Leu Val
            20                  25                  30

Xaa Xaa Ala
        35

<210> SEQ ID NO 49
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-methylglycine

<400> SEQUENCE: 49

Gly Lys Leu Xaa Phe Phe Ala
 1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptoid
<220> FEATURE:
<221> NAME/KEY: misc_feature
<222> LOCATION: (4)..(4)
<223> OTHER INFORMATION: Xaa is N-cyclohexylmethylglycine

<400> SEQUENCE: 50

Gly Lys Leu Xaa Phe Phe Ala
 1               5
```